(12) United States Patent
Kane et al.

(10) Patent No.: US 11,324,656 B2
(45) Date of Patent: May 10, 2022

(54) METHODS AND APPARATUS FOR ADJUSTING BLOOD CIRCULATION

(71) Applicant: Avacore Technologies Inc., Ann Arbor, MI (US)

(72) Inventors: John Roy Kane, Sierra Vista, AZ (US); Scott A. Christensen, Danville, CA (US); Nathan Hamilton, Incline Village, NV (US); Stephen J. Williams, Scottsdale, AZ (US)

(73) Assignee: AVACORE TECHNOLOGIES, INC., Ann Arbor, MI (US)

( * ) Notice: Subject to any disclaimer, the term of this patent is extended or adjusted under 35 U.S.C. 154(b) by 236 days.

(21) Appl. No.: 16/569,602

(22) Filed: Sep. 12, 2019

(65) Prior Publication Data
US 2020/0000674 A1    Jan. 2, 2020

Related U.S. Application Data

(60) Continuation of application No. 15/464,273, filed on Mar. 20, 2017, now Pat. No. 10,426,694, which is a
(Continued)

(51) Int. Cl.
*A61H 9/00* (2006.01)
*A61F 7/00* (2006.01)
(Continued)

(52) U.S. Cl.
CPC .............. *A61H 9/00* (2013.01); *A61F 7/007* (2013.01); *A61F 7/02* (2013.01); *A61H 9/0078* (2013.01);
(Continued)

(58) Field of Classification Search
CPC ..................... A61H 9/0007; A61F 2007/0054
See application file for complete search history.

(56) References Cited

U.S. PATENT DOCUMENTS

| | | |
|---|---|---|
| 1,399,095 A | 12/1921 | Webb, Sr. |
| 3,217,707 A | 11/1965 | Werding |
| (Continued) | | |

FOREIGN PATENT DOCUMENTS

| | | |
|---|---|---|
| DE | 19 36 113 | 1/1971 |
| EP | 1929980 A1 | 6/2008 |
| (Continued) | | |

*Primary Examiner* — Kaitlyn E Smith
(74) *Attorney, Agent, or Firm* — Patterson & Sheridan, LLP

(57) ABSTRACT

Embodiments of the invention include a method and a device for increasing blood flow and controlling the temperature of a mammal by applying a desired pressure to extremities of a mammal. The device generally includes a pliant body element that is adapted to receive a portion of an extremity of the mammal therein, and then apply a pressure to a portion of the extremity when a pressure is provided to a region in which the extremity is positioned within the pliant body element. By evacuating the region in which the extremity is enclosed, a contact surface area between the extremity of a mammal and the pliant body element is increased, due to the external atmospheric pressure acting on the pliant body element against the skin of the extremity of the mammal. The application of pressure assures that sufficient contact and thermal heat transfer (heating or cooling) is provided to the extremity of the mammal.

17 Claims, 24 Drawing Sheets

Related U.S. Application Data continuation of application No. 15/261,676, filed on Sep. 9, 2016, now Pat. No. 10,350,134, which is a continuation of application No. 13/736,843, filed on Jan. 8, 2013, now Pat. No. 9,463,134, which is a division of application No. 11/870,780, filed on Oct. 11, 2007, now Pat. No. 8,603,150.

(60) Provisional application No. 60/868,542, filed on Dec. 4, 2006, provisional application No. 60/896,460, filed on Mar. 22, 2007.

(51) Int. Cl.
*A61F 7/02* (2006.01)
*B29C 65/04* (2006.01)
*B29L 31/00* (2006.01)

(52) U.S. Cl.
CPC .............. *A61F 2007/0029* (2013.01); *A61F 2007/0036* (2013.01); *A61F 2007/0039* (2013.01); *A61F 2007/0045* (2013.01); *A61F 2007/0054* (2013.01); *A61F 2007/0071* (2013.01); *A61F 2007/0086* (2013.01); *A61H 9/0007* (2013.01); *A61H 2201/0207* (2013.01); *A61H 2201/0228* (2013.01); *A61H 2201/10* (2013.01); *A61H 2201/164* (2013.01); *A61H 2201/1635* (2013.01); *A61H 2205/065* (2013.01); *A61H 2209/00* (2013.01); *B29C 65/04* (2013.01); *B29K 2995/0082* (2013.01); *B29L 2031/753* (2013.01)

(56) References Cited

U.S. PATENT DOCUMENTS

| | | |
|---|---|---|
| 3,507,321 A | 4/1970 | Palma |
| 3,859,989 A | 1/1975 | Spielberg |
| 3,878,839 A | 4/1975 | Norton et al. |
| 3,894,213 A | 7/1975 | Agarwala |
| 4,149,541 A | 4/1979 | Gammons et al. |
| 4,186,294 A | 1/1980 | Bender |
| 4,204,547 A | 5/1980 | Allocca |
| 4,338,944 A | 7/1982 | Arkans |
| 4,523,594 A | 6/1985 | Kuznetz |
| 4,530,350 A | 7/1985 | Brown et al. |
| 4,624,244 A | 11/1986 | Taheri |
| 4,648,392 A | 3/1987 | Cartier et al. |
| 4,658,823 A | 4/1987 | Beddoe et al. |
| 4,844,072 A | 7/1989 | French et al. |
| 5,035,003 A | 7/1991 | Rinehart |
| 5,050,613 A | 9/1991 | Newman et al. |
| 5,074,285 A | 12/1991 | Wright |
| 5,149,331 A | 9/1992 | Ferdman et al. |
| 5,183,039 A | 2/1993 | Sarian et al. |
| 5,230,333 A | 7/1993 | Yates et al. |
| 5,241,951 A | 9/1993 | Mason et al. |
| 5,241,958 A | 9/1993 | Noeldner |
| 5,314,455 A | 5/1994 | Johnson, Jr. et al. |
| 5,330,519 A | 7/1994 | Mason et al. |
| 5,344,436 A | 9/1994 | Fontenot et al. |
| 5,369,807 A | 12/1994 | Cho et al. |
| 5,417,720 A | 5/1995 | Mason |
| 5,437,610 A | 8/1995 | Cariapa et al. |
| 5,441,477 A | 8/1995 | Hargest |
| 5,476,490 A | 12/1995 | Silver |
| 5,507,792 A | 4/1996 | Mason et al. |
| 5,575,762 A | 11/1996 | Peeler et al. |
| 5,620,621 A | 4/1997 | Sontag |
| 5,634,889 A | 6/1997 | Gardner et al. |
| 5,649,954 A | 7/1997 | McEwen |
| 5,662,695 A | 9/1997 | Mason et al. |
| 5,683,428 A | 11/1997 | Franberg et al. |
| 5,683,438 A * | 11/1997 | Grahn ............... A61F 7/02 126/204 |
| 5,688,225 A | 11/1997 | Walker |
| 5,729,653 A | 3/1998 | Magliochetti et al. |
| 5,746,213 A | 5/1998 | Marks |
| 5,755,756 A | 5/1998 | Freedman, Jr. et al. |
| 5,865,841 A | 2/1999 | Kolen et al. |
| 5,868,690 A | 2/1999 | Eischen, Sr. |
| 5,913,886 A | 6/1999 | Soloman |
| 5,951,949 A | 9/1999 | Olsen |
| 5,960,475 A | 10/1999 | Fewtrell |
| 5,980,561 A | 11/1999 | Kolen et al. |
| 5,997,816 A | 12/1999 | McIntosh et al. |
| 6,144,444 A | 11/2000 | Haworth et al. |
| 6,149,674 A | 11/2000 | Borders |
| 6,197,045 B1 | 3/2001 | Carson |
| 6,226,552 B1 | 5/2001 | Staunton et al. |
| 6,238,427 B1 | 5/2001 | Matta |
| 6,245,094 B1 | 6/2001 | Pompei |
| 6,268,595 B1 | 7/2001 | Haenel |
| 6,277,143 B1 | 8/2001 | Klatz et al. |
| 6,286,144 B1 | 9/2001 | Henderson et al. |
| 6,296,617 B1 | 10/2001 | Peeler et al. |
| 6,319,214 B1 | 11/2001 | Wortman et al. |
| 6,352,550 B1 | 3/2002 | Gildersleeve et al. |
| 6,375,674 B1 | 4/2002 | Carson |
| 6,440,093 B1 | 8/2002 | McEwen et al. |
| 6,446,512 B2 | 9/2002 | Zimmerman et al. |
| 6,461,379 B1 | 10/2002 | Carson et al. |
| 6,488,643 B1 | 12/2002 | Tumey et al. |
| 6,517,510 B1 | 2/2003 | Stewart et al. |
| 6,557,704 B1 | 5/2003 | Randolph |
| 6,565,593 B2 | 5/2003 | Diana |
| 6,576,003 B2 | 6/2003 | Kotack |
| 6,581,400 B2 | 6/2003 | Augustine et al. |
| 6,602,277 B2 | 8/2003 | Grahn et al. |
| 6,620,187 B2 | 9/2003 | Carson et al. |
| 6,645,232 B2 | 11/2003 | Carson |
| 6,648,905 B2 | 11/2003 | Hoglund et al. |
| 6,656,208 B2 | 12/2003 | Grahn et al. |
| 6,660,027 B2 | 12/2003 | Gruszecki et al. |
| 6,666,879 B2 | 12/2003 | Arnold et al. |
| 6,669,715 B2 | 12/2003 | Hoglund et al. |
| D485,338 S | 1/2004 | Augustine et al. |
| 6,673,099 B2 | 1/2004 | Grahn et al. |
| 6,679,432 B1 | 1/2004 | Arnold |
| 6,692,518 B2 | 2/2004 | Carson |
| 6,695,872 B2 | 2/2004 | Elkins |
| 6,699,267 B2 | 3/2004 | Voorhees et al. |
| 6,718,785 B2 | 4/2004 | Bieberich |
| 6,763,728 B1 | 7/2004 | Albrecht |
| 6,764,502 B2 | 7/2004 | Bieberich |
| 6,775,473 B2 | 8/2004 | Augustine et al. |
| 6,786,879 B1 | 9/2004 | Bolam et al. |
| 6,802,855 B2 | 10/2004 | Ellingboe et al. |
| 6,827,728 B2 | 12/2004 | Ellingboe et al. |
| 6,830,049 B2 | 12/2004 | Augustine et al. |
| 6,840,915 B2 | 1/2005 | Augustine |
| 6,846,322 B2 | 1/2005 | Kane et al. |
| 6,855,158 B2 | 2/2005 | Stolpmann |
| 6,876,884 B2 | 4/2005 | Hansen et al. |
| 6,921,374 B2 | 7/2005 | Augustine |
| 6,966,922 B2 | 11/2005 | Grahn et al. |
| 6,974,428 B2 | 12/2005 | Knutson et al. |
| 6,974,442 B2 | 12/2005 | Grahn et al. |
| 6,987,209 B2 | 1/2006 | Augustine et al. |
| 6,988,423 B2 | 1/2006 | Bolam et al. |
| 7,001,416 B2 | 2/2006 | Augustine et al. |
| 7,010,221 B2 | 3/2006 | Augustine et al. |
| 7,014,431 B2 | 3/2006 | Hansen et al. |
| 7,041,123 B2 | 5/2006 | Stapf et al. |
| 7,074,982 B2 | 7/2006 | Knutson et al. |
| 7,087,807 B2 | 8/2006 | Stapf |
| 7,090,692 B1 | 8/2006 | Augustine et al. |
| 7,100,394 B2 | 9/2006 | Bieberich et al. |
| 7,101,389 B1 | 9/2006 | Augustine et al. |
| 7,108,713 B1 | 9/2006 | Augustine |
| 7,120,951 B2 | 10/2006 | Augustine et al. |
| 7,122,046 B2 | 10/2006 | Augustine et al. |
| 7,122,047 B2 | 10/2006 | Grahn et al. |
| 7,160,316 B2 | 1/2007 | Hamilton et al. |

(56) References Cited

U.S. PATENT DOCUMENTS

| | | |
|---|---|---|
| 7,164,852 B2 | 1/2007 | Cazzini et al. |
| 7,182,776 B2 | 2/2007 | Grahn et al. |
| 7,220,273 B2 | 5/2007 | Van Duren et al. |
| 7,226,454 B2 | 6/2007 | Albrecht et al. |
| 7,232,457 B2 | 6/2007 | Schmidt et al. |
| 7,244,268 B2 | 7/2007 | Arnold et al. |
| 7,264,630 B1 | 9/2007 | Webb |
| 7,351,254 B2 | 4/2008 | Magers |
| 7,361,186 B2 | 4/2008 | Voorhees et al. |
| 7,422,576 B2 | 9/2008 | Boynton et al. |
| 8,066,752 B2 | 11/2011 | Hamilton et al. |
| 8,182,521 B2 | 5/2012 | Kane et al. |
| 8,454,671 B2 | 6/2013 | Lennox et al. |
| 2002/0007201 A1 | 1/2002 | Grahn et al. |
| 2002/0019653 A1 | 2/2002 | Grahn et al. |
| 2002/0022791 A1 | 2/2002 | Morris et al. |
| 2002/0022871 A1 | 2/2002 | Grahn et al. |
| 2002/0142894 A1 | 10/2002 | Flynn |
| 2003/0024684 A1 | 2/2003 | Lyons et al. |
| 2003/0040783 A1 | 2/2003 | Salmon |
| 2003/0097163 A1* | 5/2003 | Kane ............ A61F 7/02 607/108 |
| 2003/0125649 A1 | 7/2003 | McIntosh et al. |
| 2003/0191437 A1 | 10/2003 | Knighton et al. |
| 2004/0024322 A1 | 2/2004 | Caspers |
| 2004/0073146 A1 | 4/2004 | Weintraub et al. |
| 2004/0077978 A1 | 4/2004 | Nelson et al. |
| 2004/0106884 A1 | 6/2004 | Bolam et al. |
| 2004/0127964 A1 | 7/2004 | Grahn et al. |
| 2004/0133253 A1 | 7/2004 | Grahn et al. |
| 2004/0162571 A1 | 8/2004 | Rabiner et al. |
| 2004/0223962 A1 | 11/2004 | Riordan |
| 2004/0225341 A1 | 11/2004 | Schock et al. |
| 2004/0260369 A1 | 12/2004 | Schock et al. |
| 2005/0027218 A1 | 2/2005 | Filtvedt et al. |
| 2005/0033392 A1 | 2/2005 | Belzidsky |
| 2005/0065583 A1 | 3/2005 | Voorhees et al. |
| 2005/0070954 A1 | 3/2005 | Johnson et al. |
| 2005/0085882 A1 | 4/2005 | Grahn et al. |
| 2005/0096714 A1 | 5/2005 | Freedman et al. |
| 2005/0131489 A1 | 6/2005 | Gardon-Mollard |
| 2005/0159690 A1 | 7/2005 | Barak et al. |
| 2005/0209663 A1 | 9/2005 | Hamilton et al. |
| 2005/0209665 A1 | 9/2005 | Hunter et al. |
| 2005/0222526 A1 | 10/2005 | Perry et al. |
| 2005/0251067 A1 | 11/2005 | Terry |
| 2005/0256556 A1 | 11/2005 | Schirrmacher et al. |
| 2006/0016012 A1 | 1/2006 | Liu |
| 2006/0058858 A1 | 3/2006 | Smith |
| 2006/0074362 A1 | 4/2006 | Rousso et al. |
| 2006/0111766 A1 | 5/2006 | Grahn et al. |
| 2006/0122670 A1 | 6/2006 | Grahn et al. |
| 2006/0150792 A1 | 7/2006 | Cazzini et al. |
| 2007/0060987 A1 | 3/2007 | Grahn et al. |
| 2007/0123962 A1 | 5/2007 | Grahn et al. |
| 2007/0142887 A1 | 6/2007 | Cazzini et al. |
| 2008/0021531 A1 | 1/2008 | Kane et al. |
| 2008/0064992 A1* | 3/2008 | Stewart ............ A61H 9/0078 601/7 |
| 2008/0077205 A1 | 3/2008 | Cazzini |
| 2008/0132976 A1 | 6/2008 | Kane et al. |
| 2008/0177232 A1 | 7/2008 | Knighton et al. |
| 2008/0208088 A1 | 8/2008 | Cazzini et al. |
| 2008/0249593 A1 | 10/2008 | Cazzini et al. |
| 2009/0036959 A1 | 2/2009 | Filtvedt et al. |
| 2009/0048649 A1 | 2/2009 | Peret et al. |
| 2009/0099629 A1 | 4/2009 | Carson et al. |
| 2009/0112298 A1 | 4/2009 | Jusiak et al. |
| 2009/0177184 A1 | 7/2009 | Christensen et al. |
| 2009/0312675 A1 | 12/2009 | Sampson et al. |
| 2010/0210982 A1 | 8/2010 | Balachandran et al. |
| 2011/0021960 A1 | 1/2011 | Filtvedt et al. |
| 2011/0172749 A1 | 7/2011 | Christensen et al. |
| 2011/0238143 A1 | 9/2011 | Schock et al. |
| 2011/0264063 A1 | 10/2011 | Weston |
| 2011/0301510 A1 | 12/2011 | Filtvedt et al. |

FOREIGN PATENT DOCUMENTS

| | | |
|---|---|---|
| FR | 2544202 | 10/1984 |
| WO | 96/28120 | 9/1996 |
| WO | 98/40039 | 9/1998 |
| WO | 01/80790 | 11/2001 |
| WO | 02/085266 | 10/2002 |
| WO | 03/045289 | 6/2003 |

* cited by examiner

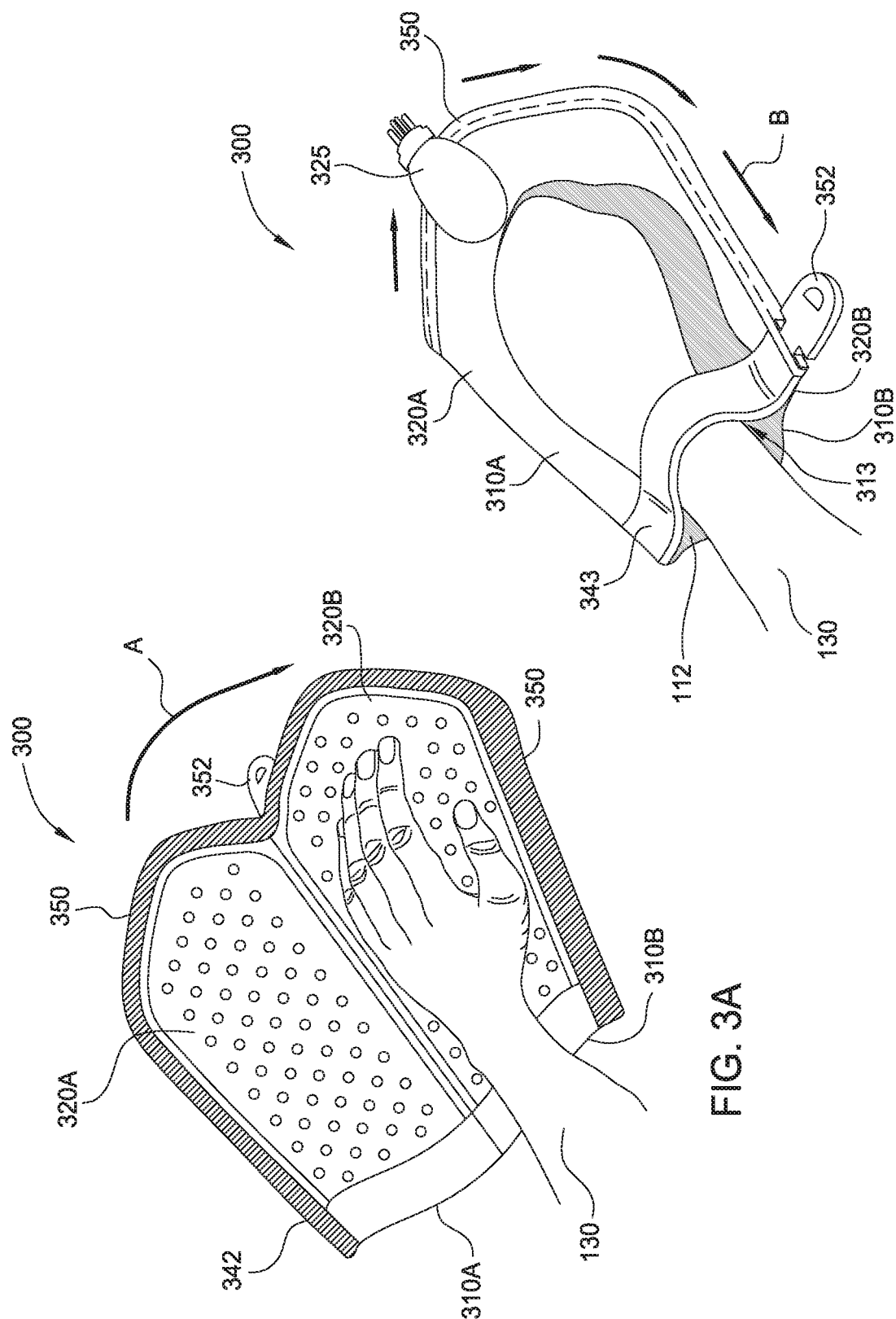

FOOT SIZE 13.5

FOOT SIZE 9.5

METHODS AND APPARATUS FOR ADJUSTING BLOOD CIRCULATION

CROSS-REFERENCE TO RELATED APPLICATIONS

This application is a continuation of pending U.S. patent application Ser. No. 15/464,273, filed on Mar. 20, 2017, which is a continuation of U.S. patent application Ser. No. 15/261,676, filed Sep. 9, 2016, which is now patented as U.S. Pat. No. 10,305,134, which is a continuation of U.S. patent application Ser. No. 13/736,843, filed Jan. 8, 2013, which is now patented as U.S. Pat. No. 9,463,134, which is a divisional of U.S. patent application Ser. No. 11/870,780, filed Oct. 11, 2007, which is now patented as U.S. Pat. No. 8,603,150, which claims the benefit of U.S. Provisional Patent Application Ser. No. 60/868,542, filed Dec. 4, 2006, and the benefit of the U.S. Provisional Patent Application Ser. No. 60/896,460, filed Mar. 22, 2007. Each of the aforementioned patents and patent applications are herein incorporated by reference.

BACKGROUND OF THE INVENTION

Field of the Invention

Embodiments of the invention generally relate to methods and apparatus for increasing blood flow and/or adjusting and maintaining the core temperature of a human.

Description of the Related Art

Homoiothermic animals, such as humans, strive to maintain relatively constant internal temperatures despite temperature variations in ambient environments and fluctuations in internal heat released as cellular metabolism byproducts. In humans, the thermal core generally includes the vital organs of the body, such as the brain and the several organs maintained within the abdomen and chest. Peripheral tissues, such as the skin, fat, and muscles, act as a buffer between the thermal core and the external environment of the animal by maintaining a temperature gradient that ranges from near-core temperature within internal organs to near-ambient temperature at the surface of the animal.

Mammalian temperature regulation requires adaptations mechanisms, such as insulation, respiratory heat conservation, and passive heat dissipation, etc., to enable mammalian survival without excessive resource expenditure to generate a stable internal thermal environment. Insulation, internal or external, impedes heat transfer from ambient condition to the body core and also protects animals from the cold. Subcutaneous insulation, similarly, retards the transfer of heat from the skin surface into the body core. The insulative properties of peripheral tissues are determined by blood flow through the tissues and in the absence of blood flow, heat transfer through the tissues is negligible. For example, lack of blood flow and poor blood perfusion makes adipose tissues good insulators. Any tissues that are poorly perfused may become insulators. Tissue blood perfusion determines local heat transfer and enables delivery of heat to (or removal from) a body region.

Respiratory heat conservation is an adaptive mechanism to prevent heat loss, heat exchange between the circulating blood and the air at the gas exchange surface of the lung alveoli in mammals. All of the circulating blood passes through the gas exchange surfaces of the lungs.

Heat is dissipated to the environment from the thermal core to the body surface by delivering through blood flow within the confines of the circulatory system. The distribution of the systemic blood is in accordance with local tissue metabolic demand. All blood passes through the chambers of the heart and the lungs. Cardiac output in a resting human is about 5 L/min so that the total blood volume circulates at a turnover rate of one cycle per minute. Blood volume and cardiac output in mammals are insufficient to uniformly perfuse all tissues in the body. Specialized vascular structures promote heat exchange in the blood flow.

Two types of vascular structures are found in mammals: nutrient vascular units and heat exchange vascular units. Their functions are mutually exclusive: The nutrient vascular units contain thin-walled, small diameter blood vessels uniformly distributed throughout the skin, such as arterioles, capillaries, and venules, and require slow blood flow through to provide nutrients to local tissues. The heat exchange vascular units contain thick-walled, large diameter venules, such as venous plexuses and Arteriovenous Anastomoses (AVAs; vascular communications between small arteries and the venous plexuses), and require flowing of large blood volumes to promote heat dissipation. In humans, the venous plexuses and AVAs of the heat exchange vascular units in humans are found mainly in the non-insulated palms of the hands, soles of the feet, ears, and non hairy regions of the face.

The thermoregulatory system in homoiothermic animals can be compromised (e.g., by anesthesia, trauma, or other factors) and may lead to the various thermal maladies and diseases. Under general anesthesia, a patient may be induced to loss the ability to conserve bodily heat. Thermal maladies, such as hypothermia and hyperthermia, can occur when the thermoregulatory system is overwhelmed by severe environmental conditions. Constriction of the AVAs thermally isolates the body core from the environment, while, dilation of the AVAs promotes a free exchange of heat between the body core and the environment.

Blood flow through the heat exchange vascular structures can be extremely variable, for example, high volume of blood flow during heat stress or hyperthermia can be increase to as high as 60% of the total cardiac output. Hypothermia, on the other hand, is the result of prolonged exposure to a cold challenge where blood flow through the venous plexuses and AVAs can be near zero of the total cardiac output. Vasoconstriction of the peripheral blood vessels may arise under hypothermia in order to prevent further heat loss by limiting blood flow to the extremities and reducing heat transfer away from the thermal core of the body. However, vasoconstriction makes it much more difficult to reverse a hypothermic state since vasoconstriction impedes the transfer of heat from the body surface to the thermal core and makes it difficult to simply apply heat to the surface of the body. This physiological impediment to heat transfer is referred to as a vasoconstrictive blockade to heat exchange. There is a need to regulate blood flow to the venous plexuses and AVAs of the heat exchange vascular units and intervene thermal maladies.

Other thermal malady related diseases, such as venous thromboembolic disease, continues to cause significant morbidity and mortality. Hospitalization due to venous thrombosis and pulmonary embolism (PE) ranges from 300,000 to 600,000 persons a year. Following various types of surgical procedures, as well as trauma and neurological disorders, patients are prone to developing deep vein thrombosis (DVT) and PE, which usually originate from blood clots in the veins and some clots traveling to the lung. Regardless of the original reasons for hospitalization, one in a hundred patients upon admission to hospitals nationwide dies of PE. Patients suffering from hip, tibia and knee fractures undergoing orthopedic surgery, spinal cord injury, or stroke are especially at high risk. Thus, prevention of DVT and PE is clinically important.

It is believed that slowing of the blood flow or blood return system from the legs may be a primary factor related to DVT with greatest effect during the intraoperative phase. Also of concern is the postoperative period. Even individuals immobilized during prolong travel on an airplane or automobile may be at risk. Generally, without mobility, return of the blood back to heart is slowed and the veins of an individual rely only on vasomotor tone and/or limited contraction of soft muscles to pump blood back to the heart. One study shows that travel trips as short as three to four hours can induce DVT and PE.

Current approaches to prophylaxis include anticoagulation therapy and mechanical compression to apply pressure on the muscles through pneumatic compression devices. Anticoagulation therapy requires blood thinning drugs to clear clots in the veins which must be taken several days in advance to be effective. In addition, these drugs carry the risk of bleeding complications. Pneumatic compression devices, which mechanically compress and directly apply positive message-type pressures to muscles in the calf and foot sequentially, are not comfortable, are difficult to use even in a hospital, and are too cumbersome for mobile patients or for use during prolonged travel. In addition, most of them are heavy weighted and there are no portable or user friendly devices.

U.S. Pat. No. 5,683,438, issued to Grahn and assigned to Stanford University, discloses an apparatus and method for overcoming the vasoconstrictive blockade to heat exchange by mechanically distending blood vessels in a body portion and providing heat transfer to the body core of a hypothermic mammal. The disclosed device comprises a fluid-filled heating blanket that is lodged within a tubular, elongated hard shelled sleeve placed over the body portion. Sub-atmospheric pressure is applied and maintained within the sleeve. However, most devices for regulating body temperature may not provide sufficient heat or adequate surface area for heat transfer being optimized and evenly distributed between the heating element and the body of the patient. In addition, the devices may not be able to adapt to the variability in patient sizes or provide mobility of the body portion during prolong treatment.

Therefore, there remains a need for an apparatus and method to increase blood flow to the venous plexuses and AVAs of the heat exchange vascular units, thereby reducing the vasoconstrictive blockade and promoting heat exchange for body temperature regulation and disease intervention.

SUMMARY OF THE INVENTION

Embodiments of the invention provide methods and apparatus for increasing blood flow and/or controlling body temperature which can be used in regulating body temperature to prevent and/or intervene thermal maladies, deep vein thrombosis, PE and other disease arising from a compromised thermal regulatory system inside a mammal. In one embodiment, a flexible extremity device is provided for regulating temperature and/or providing a vacuum or a negative pressure on an extremity of a mammal, such as a hand, an arm, a leg, foot, or calf of a leg, in order to increase blood flow on the extremity. According to an embodiment of the invention, the flexible extremity device can be used in combination with a mechanical compression device or the flexible extremity device can itself be modified to include one or more pressure-applying gas plenums in order to apply pressurized compression forces to an extremity of a mammal, in addition to regulating the temperature and/or applying vacuum to the extremity.

Embodiments of the invention provide a device for increasing blood flow and controlling body temperature, comprising a body element having one or more walls that enclose an internal region, an opening formed in the body element that is adapted to receive an extremity of a mammal and allow a portion of the extremity to be positioned within the internal region, one or more thermal exchanging units that are disposed in the internal region, and a pump that is adapted to control the pressure within the internal region to improve the thermal contact between the one or more thermal exchange units and the surface of the portion of the extremity.

Embodiments of the invention may further provide a device for increasing blood flow and controlling body temperature in a mammal, comprising a body element having one or more walls that enclose an internal region, an opening formed in the body element that is adapted to receive an extremity of a mammal and allow a portion of the extremity to be positioned within the internal region, one or more thermal exchanging units that are disposed in the internal region, a manifold having a first fittings that is in fluid communication with the internal region and a second fitting that is in fluid communication with a fluid plenum formed in one of the one or more thermal exchanging units, and a controller system comprising a first pump that is adapted to control the pressure within the internal region when it is in fluid communication with the first fitting, a fluid heat changer having a thermal exchanging fluid that is adapted to control the temperature of the one or more thermal exchanging units when it is in fluid communication with the one or more thermal exchanging units, a pressure sensor that is in fluid communication with the internal region, a temperature sensor that is adapted to measure a temperature of the mammal, and a controller that is adapted to control the temperature of the fluid heat exchanging fluid and the pressure of the internal region using inputs received from the temperature sensor and the pressure sensor, and control the first pump.

Embodiments of the invention may further provide a method of increasing blood flow and controlling body temperature in a mammal, comprising positioning an extremity of a mammal in an internal region that is formed using one or more walls of a body element, disposing one or more thermal exchanging units on a surface of the extremity that is positioned within the internal region, controlling the temperature of the one or more thermal exchange units, and adjusting the pressure in the internal region to cause one of the one or more walls to urge at least one of the one or more thermal exchange units against the surface of the extremity.

Embodiments of the invention may further provide a method of preventing DVT includes providing a flexible lower extremity device to a mammal, the lower extremity device comprising one or more collapsible and pliant body elements which are capable of expanding from a minimized first volume into an expanded second volume for containing a portion of an extremity of a mammal therein and reducing from the expanded second volume into a pressurized third volume to conformably enclose the portion of the lower extremity, regulating the temperature of the lower extremity using the lower extremity device, vasodilating an Arteriovenous Anastomoses (AVAs) blood vessel of the lower extremity of the mammal, and reducing the constriction of the AVA blood vessel using the lower extremity device, thereby increasing blood flow of the lower extremity and decreasing clotting within the veins. The method can further include applying mechanical compression to the lower extremity of the mammal. The method may optionally include reducing the pressure of the chamber of the lower extremity device, such as to vacuum levels.

In a further embodiment, a method of increasing blood flow includes regulating the temperature of one or more extremities of a mammal and exposing the one or more extremities to a vacuum or a reduced pressure environment.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

FIG. 3A is a perspective view of yet another exemplary device which is not yet folded nor enclosed according to one embodiment of the invention.

FIG. 3B is a perspective view of the exemplary device of FIG. 3A which is folded and enclosed according to one embodiment of the invention.

DETAILED DESCRIPTION OF THE INVENTION

Figure 1A:
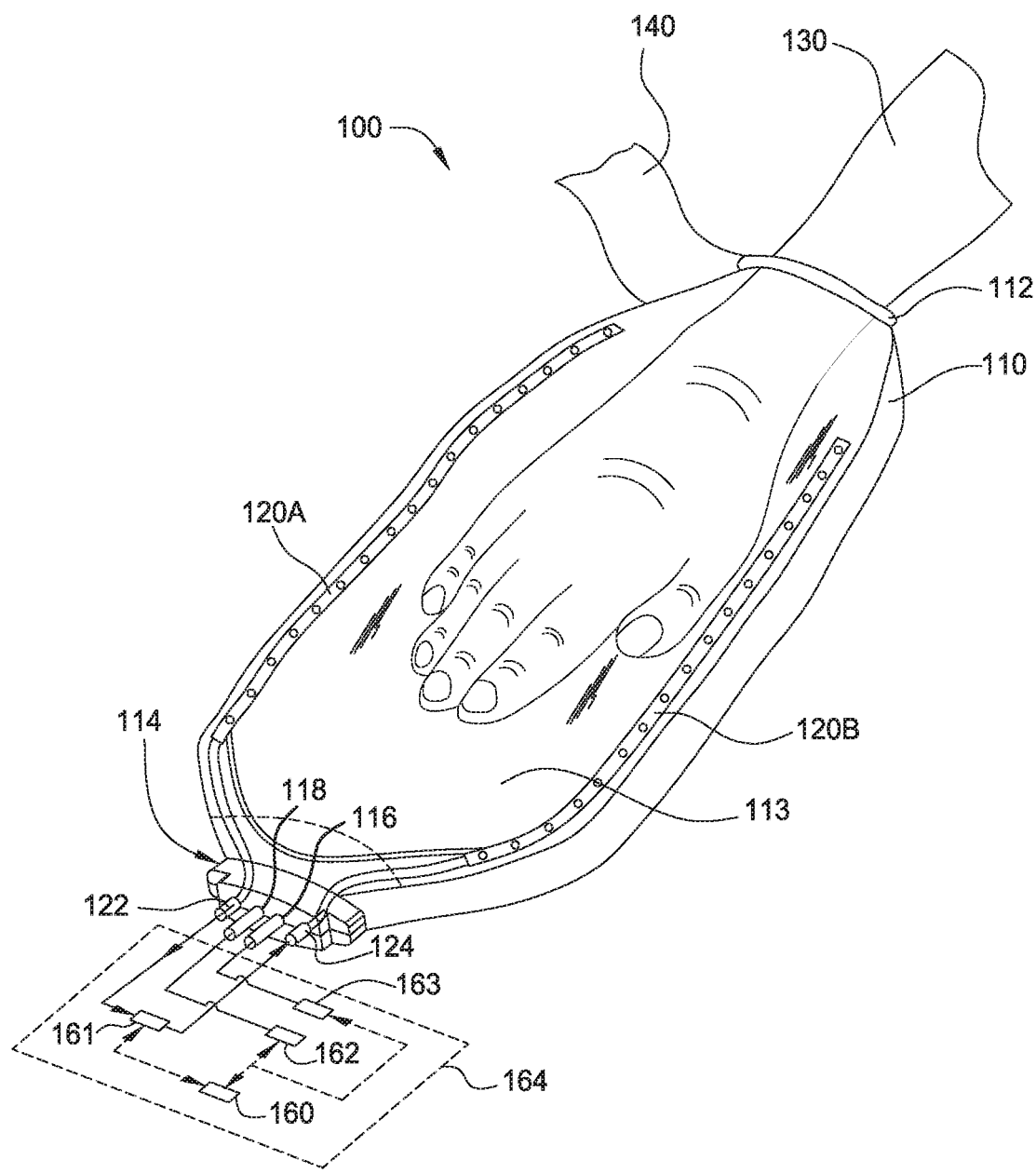
FIG. 1A is a cross-sectional view of one embodiment of an exemplary device according to one embodiment of the invention.

Embodiments of the invention include a method and a device for increasing blood flow and controlling the temperature of a mammal by applying a desired pressure to extremities of a mammal. The device generally includes one or more collapsible and pliant body elements, capable of expanding from a first volume into an expanded second volume so the device can receive a portion of an extremity of the mammal therein and then be reduced from the expanded second volume into a pressurized third volume to conformably enclose the portion of the extremity. One or more thermal exchange units can be positioned in the one or more collapsible and pliant body elements. Accordingly, the temperature of the extremity of a mammal can be regulated by providing a heated or cooled fluid medium or electric thermal energy to the one or more thermal exchange units. Next, by evacuating the region in which the extremity is enclosed the contact surface area between the extremity of a mammal and the one or more thermal exchange units is increased, due to the external atmospheric pressure acting on the pliant body elements against the skin of the extremity of the mammal. The application of pressure assures that sufficient contact and thermal heat transfer (heating or cooling) is provided to the extremity of the mammal. By controlling the application of pressure to the mammal's extremity that is positioned within the enclosed region of the one or more collapsible and pliant body elements skin perfusion can be improved. The pressure that is applied to the region surrounding the extremity can be adjusted to increase the blood perfusion at the skin surface of the extremity, and also improve heat transfer to the blood and rest of the body. It is believed that regulating the pressure in the region around the mammal's extremity to allow an eternal pressure (e.g., atmospheric pressure) or force to create a contact pressure between the device components (e.g., thermal exchange units) and the extremity of about 13.5 mmHg will provide a desirable increase of blood perfusion. It is also believed that the exposure of the skin of the extremity to a sub-atmospheric pressure environment can also help the vasodilatation of the vasculature in the mammal's extremity. The vasodilatation of the vasculature may also help to increase the thermal exchange between the one or more thermal exchange units and the mammal's extremity.

The extremity can be any kinds of the extremity of a mammal, such as an arm, a hand, a forearm, a forearm with an elbow, a hand with a wrist, a limb, a foot, a leg, a calf, an ankle, toes, etc., where Arteriovenous Anastomoses (AVAs) are located and/or when increased blood flow is desired. Arteriovenous Anastomoses (AVAs), which are connected to arteries and veins, are specialized blood vessels located primarily in the palms and fingers of the hands, the soles and toes of the feet, the cheeks, and the ears, etc. It is recognized that the device described herein may be adapted for use with other extremities that have vasculature structures suitable for the increasing blood flow methods described herein. Regulating the temperature of the mammal's extremity may include elevating, cooling, and/or maintaining the mammal's temperature. The mammal may be a human or other mammal. People at high risk of DVT, PE and other conditions, such as edema, wound swelling, venous stasis ulcers, diabetic wounds, decubitous ulcer, orthopedic surgery patients, spinal cord injured individuals, among others, can benefit from the invention.

According to one or more embodiments of the invention, devices and methods are provided to intervene thermal maladies (e.g., hypothermia and hyperthermia, etc.), to regulate the temperature of the extremity of a mammal when the thermoregulatory system of the mammal is compromised (e.g., by general anesthesia, local anesthesia, trauma, post-surgery conditions, or other factors), and/or to prevent deep vein thrombosis (DVT), pulmonary embolism (PE), and other diseases. The devices and methods as described herein are tested to be able to increase blood flow in the extremity of the mammal, which may include an appendage. Experiments performed on humans that have diabetes indicate that optimal pressure to increase blood flow could be about 13-14 mmHg, but that pressures between 1 and 80 mmHg, and more preferably 3 and 40 mmHg and more preferably 5 and 20 mmHg can increase blood perfusion. Pressures of approximately 14 mmHg combined with appropriate heat can increase blood flow, as a percent per minute of the volume of the appendage (in this case an arm) from a base level of between about 4% per minute to an increased level of about 8% per minute. The pressure applied to the skin by the device can be used to increase blood flow, which can be accomplished by a variety of methods including, but not limited to using atmospheric pressure to collapse a bag that has been evacuated or by pressurizing, or inflating, a cuff that encompasses a significant portion of appendage (FIG. 6G). Some results and embodiments are discussed below.

In one embodiment, a device for increasing blood flow and preventing deep vein thrombosis (DVT) is provided to a mammal's extremity by using atmospheric pressure outside the enclosed extremity to increase the surface area of the contact between the skin of the mammal's extremity and one or more thermal exchange units to improve profusion, and by regulating the temperature of the mammal's extremity by controlling the temperature of the thermal exchange units. In this case, the external atmospheric pressure is used to press the one or more thermal exchange units against the mammal's extremity to provide as much thermal exchange as possible, and increasing the blood flow of the mammal's extremity. In particular, the invention provides a non-invasive, convenient apparatus for efficiently adjusting the temperature, applying vacuum, and/or applying compression pressure or forces, to the mammal's extremity to increase blood flow, promote venous blood return, prevent clots in the veins, and prevent DV, among others.

Figure 1B:
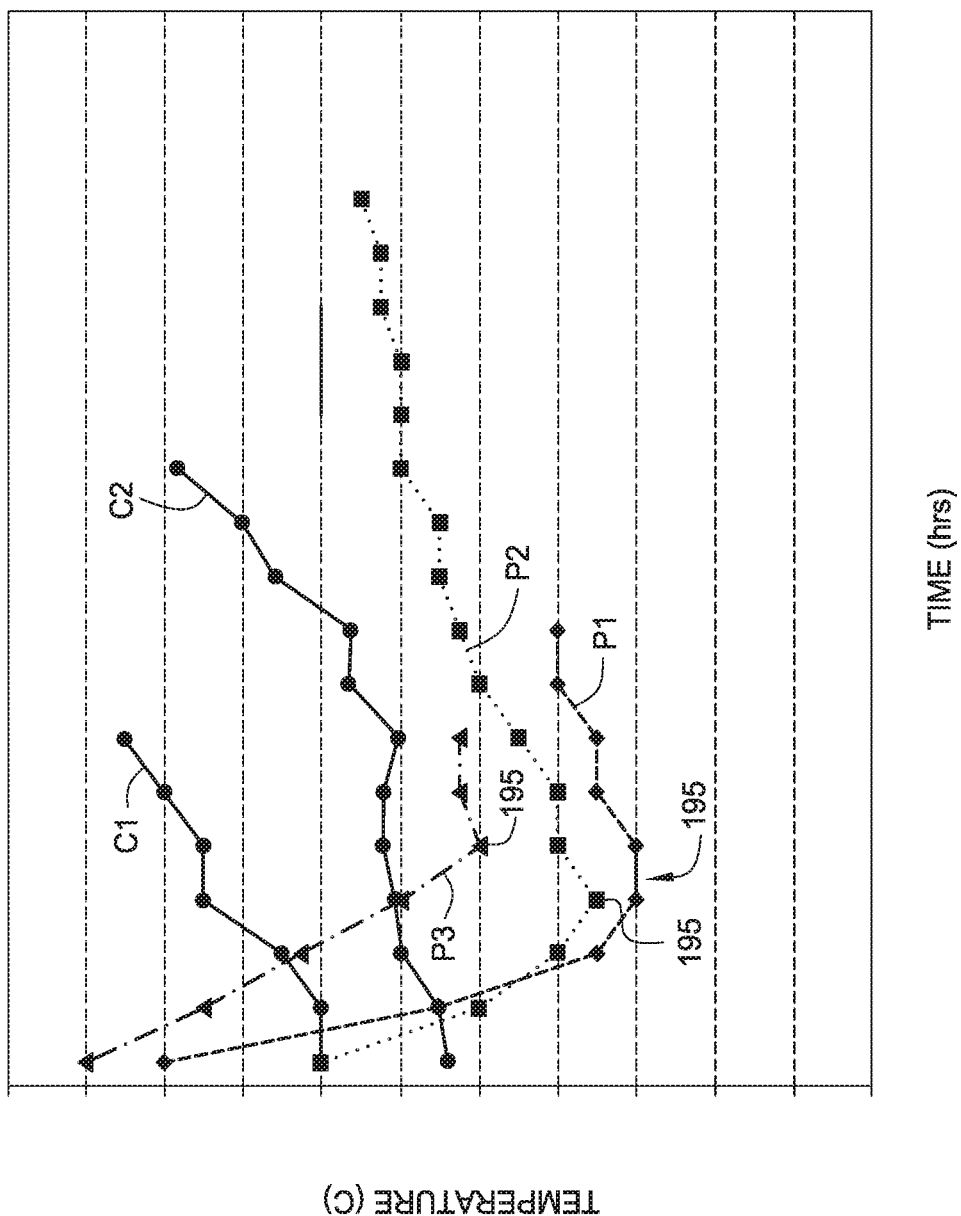
FIG. 1B is graph demonstrating the results of increased blood flow using the device according to one embodiment of the invention.

FIG. 1A is a cross-sectional view of one embodiment of a device 100 that is used to increasing blood flow by transferring heat to a mammal's extremity. The device transfers heat to and/or from a mammal's extremity, such as an arm, a hand, a forearm, a forearm with an elbow, a hand with a wrist, a limb, a foot, a leg, a calf, an ankle, toes, etc., where AVAs are located to provide an improved and efficient control of the patients temperature, and blood flow in the extremity. FIG. 1B illustrates plots of the core temperature of a patent as a function of time using various different methods to increase the temperature of the patient's core. Curves P1, P2 and P3 illustrate the published results received using conventional techniques, such as convective heat transfer processes that exchange heat with the skin of the patient by delivering a flow of heated or cooled air. Curves C1 and C2 illustrate the results received using the devices discussed herein, for example, device 100 illustrated in FIG. 1A. One characteristic feature of the conventional schemes illustrated by the curves P1, P2 and P3 is the unwanted and immediate decrease in temperature of the patient for a period of time before a minimum temperature 195 is reached, and the patient's temperature finally starts to increase. It is believed that the initial decrease in temperature found using conventional convective heat transfer techniques illustrated in curves P1, P2, and P3 is undesirable and uncomfortable to the patient, since it generally causes or doesn't quickly eliminate shivering of the patient. In contrast, as shown in curves C1 and C2, the devices discussed herein will have the characteristic of a generally increasing core temperature from the start and doesn't have the inefficient and uncomfortable effect found in current conventional devices, due to the novel method of enclosing the patient's extremity, adjusting the pressure surrounding the extremity within the enclosure, increasing blood perfusion by controlling the contact pressure, and improving the thermal contact with a thermal heat exchanging device (e.g., conductive heat transfer), as discussed below.

FIG. 1A is a cross-sectional view of one embodiment of a device 100 having one or more thermal exchange units 120A, 120B. The device 100 includes an opening 112 formed in one or more body elements 110 that is used to enclose and receive a portion of an extremity 130 of a mammal. The device 100 may also contain a sealing element 140 that is attached to the opening 112, which is used to form a seal around the extremity 130. The enclosed extremity 130 positioned within the internal region 113 of the device 100 can then be evacuated to allow the atmospheric pressure external to the one or more body elements 110 to urge the one or more thermal exchange units 120A, 120B against the extremity 130 to provide a desired thermal exchange. Also, by enclosing the extremity 130 the thermal environment formed around the extremity can help to improve the control of the temperature and heat exchange between thermal exchange units and the extremity.

The body element 110 is generally designed so that it will occupy a minimum amount of space, or volume, so that it can be easily and conveniently folded, stored, or shipped. The body element 110 is generally capable of being expanded from a minimized volume into an expanded volume for containing a portion of an extremity of a mammal therein. Under a pressurized condition, the volume or space of the body element 110 may be reduced from the expanded volume into a pressurized volume or space, such as a volume that conformally encloses the portion of the extremity 130. It is generally desirable to use a body element 110 that is flexible enough to allow the pressure applied to each and every portion of the extremity 130 enclosed inside the device 100 to be evenly and equally distributed. In general, the minimized volume and the expanded volume are maintained under atmospheric pressure.

Embodiments of the invention provide subjecting portions of an extremity of a mammal to a reduced pressure environment, preferably under vacuum or a negative pressure to increase contact surface area for thermal regulation, and adjusting the temperature of the extremity of the mammal, thereby increasing blood flow. Under a reduced pressure inside the device 100, the portions of the body element 110 are pressed against extremity 130. The pressure inside the internal region 113 of the pressurized volume of the body element 110 of the device 100 can be regulated to a level lower than atmospheric pressure, such as a pressure level of about 0 mmHg to about −80 mmHg by use of a pump 163 (e.g., mechanical pump). In another example, it is desirable to regulate the pressure in the internal region 113 to a pressure between about −10 mmHg to about −14 mmHg. In another example, it is desirable to regulate the pressure in the internal region 113 to a pressure between about −10 mmHg to about −13.5 mmHg.

The body element 110 is comprised of a collapsible and pliant material, including but not limited to, urethane, polyurethane, polypropylenes, polystyrenes, high density polyethylene's (HDPE), low density polyethylene's (LDPE), poly(vinyl chloride), rubbers, elastomers, polymeric materials, composite materials, among others. For example, the body element 110 can be made of disposable low cost materials. The collapsible and pliant material may comprise any suitable flexible material, for example, gas permeable thermoplastics, elastomeric materials, such as C-FLEX™ from Consolidated Polymer Technologies, Inc. (Largo, Fla.), DynaFlex from GLS Corporation (McHenry, Ill.), materials available from Argotec (Greenfield, Mass.), and other elastomeric materials with similar properties. In one embodiment, the collapsible and pliant material comprises a material that is temperature resistant. The body element 110 can also be made of a biocompatible or hypo allergic material (and therefore safe for contact with the skin of a mammal), alternatively, the body element can be made of a transparent or semi-transparent material that allows viewing of the extremity 130 positioned therein. As another example, the body element 110 may be made of materials that may be sterilized via autoclaving or ethylene oxide sterilization. This is especially important if the device is used during surgery where sterile conditions are very important. The thickness of the collapsible and pliant material is not limited as long as it can sustain the pressurized conditions when the device 100 is used. In one example, a urethane material having a thickness from about 1.5 mils to about 12 mils can be used to pliantly conform to the shape and size of the portion of the extremity 130 contained therein. In general, the thickness of the collapsible and pliant material is not limited as long as it is compliant enough to substantially conform to the extremity and can sustain the desired pressurized conditions when the device 100 is in use.

The one or more thermal exchange units 120A, 120B can be attached to one or more portions of the body element 110 and adapted to contact the portion of the extremity 130 under pressurized conditions and to increase, reduce, or maintain the temperature of the extremity 130 received therein. The thermal exchange unit 120A, 120B can be permanently or detachably placed inside the device 100 to provide thermal exchange for the extremity 130 received therein. Examples of some exemplary thermal exchange units 120A, 120B are illustrated and further discussed in conjunction with FIGS. 5A-5B.

A thermal-exchange fluid medium, such as heated fluid, heated air, cooled fluid, or cooled air, etc., can be provided from a fluid source 161 into the thermal exchange units 120A, 120B via one or more fluid supply lines 124 and out of the device 100 via one or more fluid return lines 122. The temperature of the one or more thermal exchange units positioned in the device 100 may also be controlled by use of an electric pad, fluid type heat exchanging device, or any other suitable thermal exchange units, that are used individually or in combination. Thermal energy can be transferred from the thermal exchange unit to the extremity 130 during heating or from the extremity 130 to the one or more thermal exchange units during the process of cooling the extremity 130. For example, the thermal exchange units 120A, 120B may be a fluid heating pad having, for example, heated water delivered there through using a recirculation type heat exchanging system. As another example, the thermal exchange units 120A, 120B may be a pad having chemicals therein for heating or cooling. Alternatively, the thermal exchange units 120A, 120B may include an electric pad, as described in detail in co-pending U.S. provisional patent application Ser. No. 60/821,201, filed Aug. 2, 2006, which is incorporated by reference herein.

Good contact with the thermal exchange units 120A, 120B is important in maximizing thermal transfer to the extremity 130. Also, it is desirable to assure that the thermal exchange unit(s) will not loose contact the extremity 130 through normal jostling or positioning of the patient. Also, optimal contact and efficient thermal exchange between the thermal exchange units and the extremity 130 can be compromised when portions of the extremity 130 become arched or deformed due to the pressure differential acting on the extremity and the exterior of the device 100 when the internal region 113 is evacuated. The contact force caused by the pressure differential is approximately equal to the contact surface area of the thermal exchange unit against the extremity 130 times the pressure differential. For example, the pressure differential may be approximately three pounds. In one embodiment, the collapsible and pliant body elements of the device helps to assure that sufficient contact between the thermal exchange units 120A, 120B and the extremity 130 is maintained if the extremity becomes arched or deforms. The surface pressure created by the external atmospheric pressure urges the thermal exchange units 120A, 120B against the extremity 130. As such, by applying a surface pressure to the extremity 130 thermal energy can be more evenly distributed to the extremity 130.

Accordingly, the materials of the body element 110 and the thermal exchange units 120A, 120B are made of a flexible material, which can be pliant and easily collapsible to conform into the shape of the extremity and securely surround and enclose the portion of the extremity 130 to provide good contact between the surfaces of the extremity 130 and the thermal exchange units 120A, 120B (or the body element 110). The material for the thermal exchange units 120A, 120B and the body element 110 are comprised of collapsible and pliant material to enhance the surface contact between the thermal exchange units 120A, 120B and the extremity 130. The material of the body element 110 thus may collapse against the thermal exchange units 120A, 120B due to the sub-atmospheric pressure or a vacuum pressure level achieved in the internal region 113 of the device 100.

Figure 7:
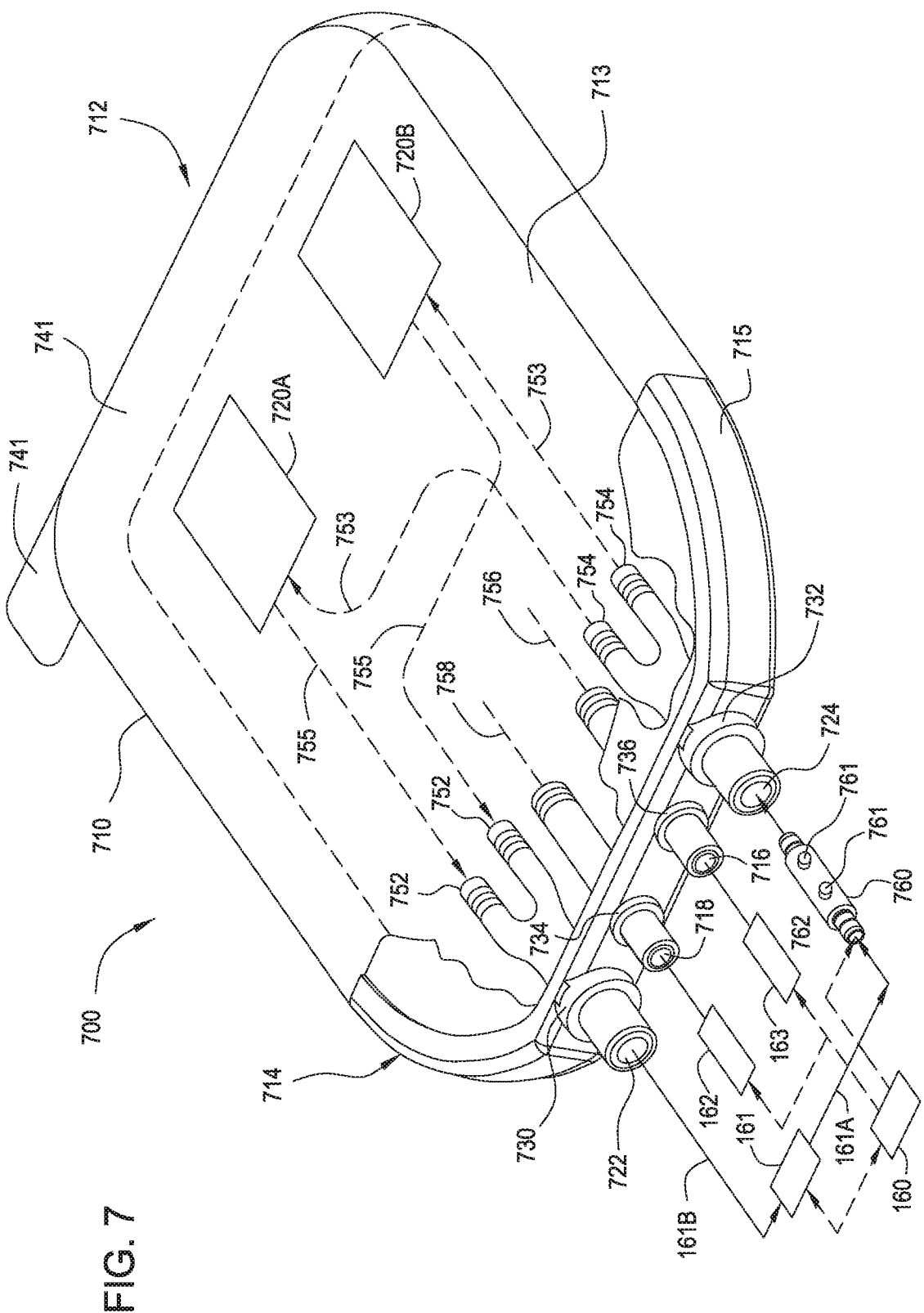
FIG. 7 illustrates an exemplary manifold with one or more fittings for tubing's according to an embodiment of the invention.

The body element 110 may include one or more apertures for attaching various fluid ports or pressure ports, such as a pressure port 116, a pressure sensing port 118, the fluid supply line 124, and the fluid return line 122. Accordingly, one or more thermal exchange supply lines (e.g., item 124) and one or more thermal exchange return lines (e.g., item 122) can be connected to one or more thermal sources (e.g., fluid source 161) through the one or more apertures formed in the body element 110. In one embodiment, a manifold 114 may be formed or disposed on a portion of the body element 110 to provide the connections between the various external components to the device 100. The pressure sensing port 118, the pressure port 116, the fluid supply line 124, and/or the fluid return line 122 may be covered by protective sheaths. In one aspect, the manifold 114 contains a pressure port 116, a pressure sensing port 118, the fluid supply line 124, and the fluid return line 122 that are connected to various kinds of tubing and/or connectors to connect the various external components in the device 100 to the various components or regions positioned within the internal region 113 of the device 100. The manifold 114 may be connected to the one or more apertures, the one or more pressure ports, and the one or more thermal exchange units of the device 100. The position of the apertures for the fluid ports or pressure ports can be located near any convenient portions of the body element 110 and can be close to the manifold 114 or grouped together for passing through the body element 110 via a single aperture. One example of a manifold 114 is shown in FIG. 7 to incorporate quick connecting and disconnecting fittings.

The sealing element 140 is formed on a portion of the opening 112 and adapted to seal the portion of the extremity 130 when placed inside the internal region 113 of the body element 110 to allow a pressure to be applied to the extremity 130. The sealing element 140 may be adapted to allow a pressurized volume to be formed so that an even and equal pressure is applied on each and every position for the portion of the extremity 130 of the mammal. The sealing element 140 is generally sized and used to seal the opening according to the size of the portion of the extremity 130 of the mammal. The sealing element 140 may be made of a material that is biocompatible (and therefore safe for contact with the skin of a mammal) and capable of producing an airtight seal. In one embodiment, the sealing element 140 is detachably attached to the opening 112. In another embodiment, the sealing element 140 is comprised of a disposable material, such as a disposable liner or an insert material. For example, the material of the sealing element 140 may be hydrogel, a sticky seal material, polyurethane, urethane, among others. One example of the material is hydrogel. Another example is a PS series thermoplastic polyurethane from Deerfield Urethane, Inc. Disposable sealing materials may be manufactured and packaged such that they are sterile before use and/or hypoallergenic to meet health and safety requirements. The sealing element 140 may include an air permeable portion and/or made of a permeable membrane material or a breathable material to permit the flow of air, etc. Examples of breathable materials are available from Securon Manufacturing Ltd. or 3M Company. The permeable portion may be positioned near any portion of the body portion to provide permeable outlets, allowing the vacuum to have the proper effect on the extremity 130 and providing a barrier keeping the device 100 from contamination for the comfort of the patient.

The pressurized volume defined by the body element 110 and sealing element 140 is formed by applying a negative pressure to the pressure port 116, which can be connected to a pump 163, for reducing the pressure of the internal region 113 inside the device 100. In addition, the pressure level inside the chamber 150 can be monitored by a vacuum sensor 162 placed inside the pressurized volume or be in fluid communication or fluidly attached to the pressure sensing port 118. One or more pressure ports may also be positioned between the at least one pump 163 and the body element 110.

During operation, the sealing element 140 is wrapped around the portion of the extremity 130 of the mammal top to seal the opening 112. In one embodiment, the air inside the device 100 is pumped out via a pressure port 116 connected to a pump 163 to provide a vacuum or sub-atmospheric environment in the internal region 113 of the device 100. It is recognized that the sealing element 140 is one example of a seal that may be used with the device 100, and in some cases it may be desirable not to use a seal at all. However, it is generally desirable provide a seal to reduce the leakage and thus reduce the amount of air that must be continuously removed from the apparatus during the use of the device 100. However, a sealing element 140 that exerts too much force on the extremity 130 may reduce or eliminate the return blood flow to the body, thus reducing the effectiveness of the device, and potentially creating adverse health effects. The sealing element 140 may also be attached to the device 100 with mechanical fasteners or other fastening units, such as one or more mating rings which can snap into the device 100. Another example includes the use of a tape with a removable liner, such as 3M removable tapes, etc., which can be removed when ready to use.

In one embodiment, the sealing element 140 is a single use seal. In another embodiment, the single use sealing element 140 is attached to the device 100, and the device and the sealing element 140 are disposed of after a single use. In still another embodiment, the sealing element 140 may be removed from the device 100 and the device may be used repeatedly with another sealing element.

In one embodiment, the sealing element 140 may comprise a strip of releasable adhesive tape ranging from 0.5 inches to 6 inches in width, e.g., a width large enough to cover the bottom of the extremity 130. The sealing element 140 may comprise an adhesive face and a backing portion. The sealing element 140 is generally long enough that when wrapped end over end around the edge of the opening 112, an overlap of about 0.5 inches or larger, such as about 2 inches, is present. The overlap is preferably not to encourage the user to wrap the sealing element 140 around the extremity too tightly and thus create a modest vacu-sealing force, e.g., less than 20 mm Hg. The material of the sealing element 140 may comprise a releasable adhesive material for attachment to a mammal extremity in some portion and a more permanent adhesive in other portions thereof for attaching the sealing element 140 to the device 100. The releasable adhesive material may be any of a wide variety of commercially available materials with high initial adhesion and a low adhesive removal force so that the sealing element 140 does not pull off hair or skin and create pain when it is removed. For example, the releasable adhesive may be a single use adhesive. In addition, the adhesive material may be thick and malleable so that it can deform or give, in order to fill gaps. Adhesives with water suspended in a polymer gel, e.g., a hydrogel, are generally effective. One example of such an adhesive is Tagaderm branded 3M adhesive (part No. 9841) which is a thin (5 mm) breathable adhesive that is typically used for covering burns and wounds. Another example is an electrocardiogram (EKG) adhesive such as 3M part No. MSX 5764, which is a thicker adhesive (25 mm). The sealing element 140 should fasten such that there is no leakage of the vacuum.

In one embodiment, the sealing element 140 has a backing that may be a thin, non-elastic, flexible material. The backing supports the adhesive and keeps it from being pulled into the opening 112 when the internal region 113 is evacuated. The backing also allows the adhesive to conform to both the shape of the extremity 130 and the shape of the opening 112, as well as to fold in on itself to fill gaps that may be present in the vacu-seal around the extremity 130. Furthermore, the backing prevents the adhesive from sticking to other surfaces. Commercially available polyethylene in thicknesses up to about 10 millimeters may be used for the backing. Polyethylene that is thicker than about 10 millimeters may limit the adhesive's ability to fold on itself and fill in gaps. The backing may also comprise any polymer that may be fabricated into a thin, non-elastic, flexible material. In one embodiment, the sealing element 140 comprises a backing has an adhesive disposed on two opposing adhesive faces to allow it to be attached to the body element 110 and the extremity 130. For example, 3M EKG adhesive products MSX 5764 contains a supportive backing in between multiple layers of adhesive. Multiple layers of backing can also be used to provide support for the sealing element 140.

The opening 112 of the device is preferably close to the size of the patient's extremity to minimize the difference in dimensions that the sealing element 140 must cover. The smallest opening size that will accommodate the range of extremity dimensions, such as foot sizes is preferred. Minimizing the opening size reduces the force on the extremity 130, which is approximately equal to the area of the opening 112 times the pressure differential. The sealing element 140 is typically able to be formed of different sizes to accommodate extremity sizes down to the size of a small adult and up to various sizes of a large adult. For example, multiple opening sizes, such as small, medium, and large may be used to accommodate a wider range of foot sizes.

Alternatively, the opening 112 may be adapted to contract within a size range of the extremity 130 without constricting blood flow to further minimize this force and make the sealing process by the sealing element 140 easier. For example, one or more strings may be used to tighten the opening 112 to the extremity 130. In another embodiment, external buckles, Velcro fasteners, and straps, among others, may also be used to surround the opening 112 of the device 150 and secure the opening 112 around the extremity 130.

In addition, one or more portions of the body element 110 may be made from transparent materials such that the functioning of the device and the condition of the extremity 130 may be monitored during use of the device. In an alternative embodiment, the body element 110 may be divided into two or more body sections to be assembled into the device 100 and secured by one or more fastening units, such as Velcro fasteners, or conventional snaps.

The device 100 may further include a control system 164 that contains a controller 160 that is connected to various parts of the device 100, including the pump 163 and vacuum sensor 162 connected to one or more of the pressure ports, the fluid source 161 connected to one or more of the fluid lines connected to the one or more thermal exchange units. The controller 160 may be adapted to regulate the functions and process performed by the device 100, including adjusting the fluid flow in and out of the thermal exchange units 120A, 120B, regulating the temperature of the thermal exchange units 120A, 120B, monitoring the pressure level inside the device 100 via one or more vacuum sensors 162, adjusting the pump 163 speed and the vacuum level inside the device 100, and monitoring the temperature of the extremity 130 received therein, among others. In one embodiment, the devices described herein may include an in-use sensor indicating that the device is in use (e.g., vacuum switch). In addition, the in-use sensor and/or controller 160 may indicate how many times the devices have been used.

According to an embodiment of the invention, the device can be used in combination with a mechanical compression device or a pressurized compression device to help pump blood through the patient's body. Alternatively, the device 100 can itself be modified to include one or more pressure-applying gas plenums positioned within or attached to the body element 110 in order to apply a compression force or positive gas pressure on the extremity 130 of a mammal, in addition to controlling the extremities temperature by delivering a thermally controlled fluid to the one or more fluid exchange units that are in contact with the extremity.

Figure 2A:
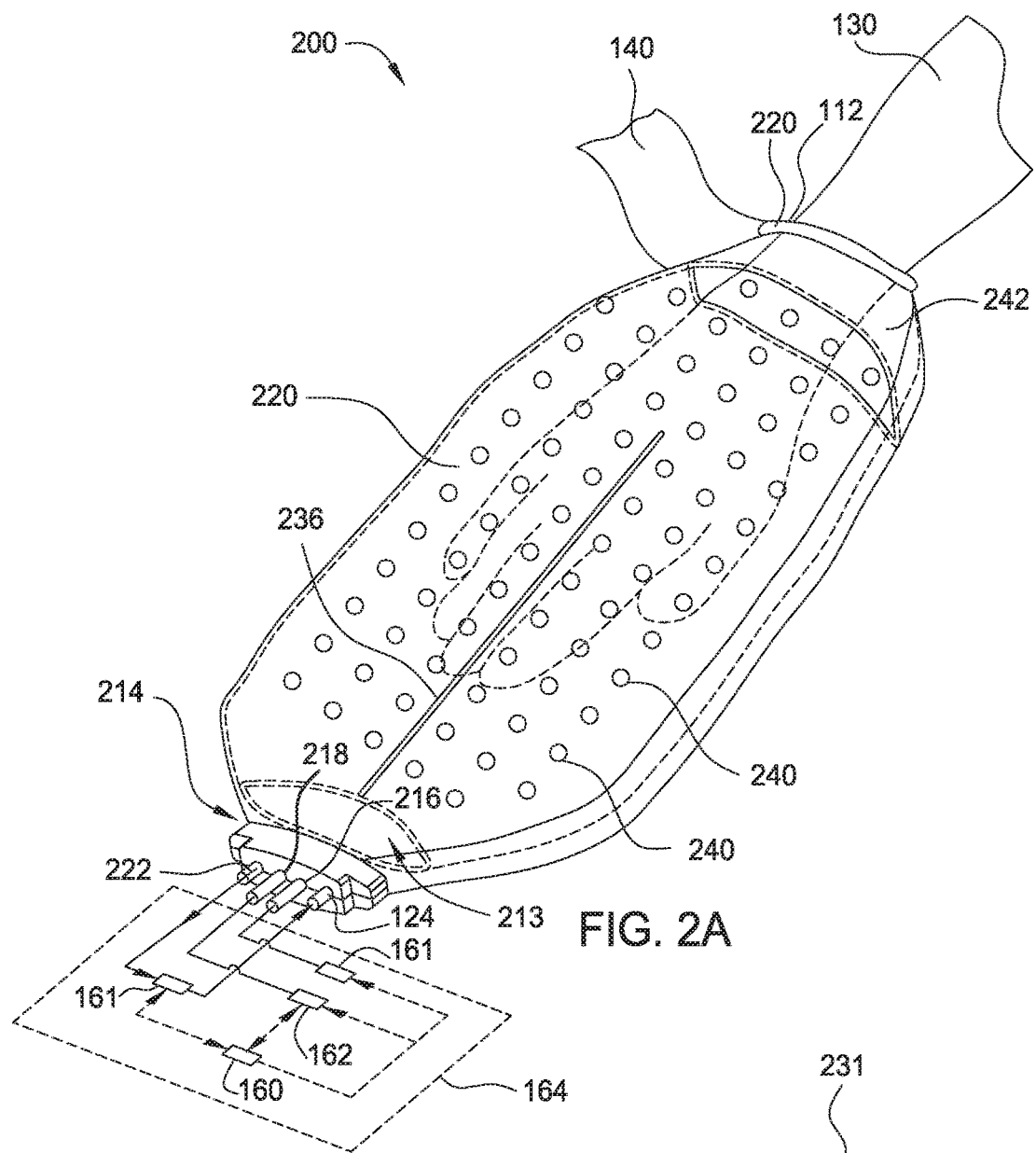
FIG. 2A is a perspective view of another exemplary device according to one embodiment of the invention.

FIG. 2A is a perspective view of another example of a device 200 according to one or more embodiments of the invention. The device 200 may include a thermal exchange unit 220, a pressure port 216, a pressure sensing line 218, a fluid supply line 224, a fluid return line 222, an opening 112 for the extremity to be enclosed therein, and a sealing element 140. A manifold 214 may be formed for providing the connection between the various fluid ports or pressure ports, such as the pressure port 216, the pressure sensing line 218, the fluid supply line 224, and the fluid return line 222, and other external components.

In one embodiment, the thermal exchange unit 220 that is permanently attached to the device 200 and composed of a collapsible and pliant material, including but not limited to, urethane, polyurethane, elastomers, polypropylenes, polystyrenes, high density polyethylene's (HDPE), low density polyethylene's (LDPE), poly(vinyl chloride), rubbers, polymeric materials, composite materials, among others. The thermal exchange unit 220 is generally designed to allow a fluid medium to be delivered there through to exchange heat with an extremity. As a result, there is no need for a separate body element (see item 110 in FIG. 1A) and thermal exchange unit 220 can be used to enclose the extremity 130 by forming a internal region 213, which can be evacuated. In addition, the body of the thermal exchange unit 220 is capable of forming into a minimized volume for folding, storage, and/or shipping. The space enclosed by the thermal exchange unit 220, or internal region 213, can also be expanded so that the extremity 130 can be disposed therein. The internal volume 213 of the thermal exchange unit 220 can be reduced under a pressurized condition to conformably apply even and equal pressure on the portion of the extremity 130 disposed inside the device 200.

The thickness of the material for the thermal exchange unit 220 is not limited as long as it is compliant enough to substantially conform to the extremity and can sustain the pressurized conditions when the device 200 is used and the fluid medium can be delivered therein. For example, a urethane material having a thickness of from about 1.5 mils to about 12 mils can be used to pliantly conform to the shape and size of the portion of the extremity 130 contained therein. Another possible material may include NTT-6000, which is a polyether polyurethane manufactured using USP Class V1 compliant materials. The NTT-6000 material can be a 2 mil gage material that is a natural color and is available from American Polyfilm, Inc. Branford, Conn. NTT-6000. Optionally, the thermal exchange unit 220 may be connected to the opening 112 through a body element 242. Alternatively, the body of the thermal exchange unit 220 can directly form the opening 112 without the use of an additional body element 242. Additionally, the device 200 may include temperature sensors to measure the fluid in and out of the thermal exchange units 200 and to measure the surface temperature of the extremity 130, such as a patient's body surface temperature.

The device 200 may further include a control system 164 having a controller 160 connected to various parts of the device 200, including the pump 163 and vacuum sensor 162 connected to one or more of the pressure ports, the fluid source 161 connected to one or more of the fluid lines connected to the one or more thermal exchange units. The controller 160 may be adapted to regulate the functions and process performed by the device 200, including adjusting the fluid flow in and out of the thermal exchange units 220, regulating the temperature of the thermal exchange units 220, monitoring the pressure level inside the device 200 via one or more vacuum sensors 162, adjusting the pump 163 speed and the vacuum level inside the device 200, and monitoring the temperature of the extremity 130 received therein, among others.

Figure 2B:
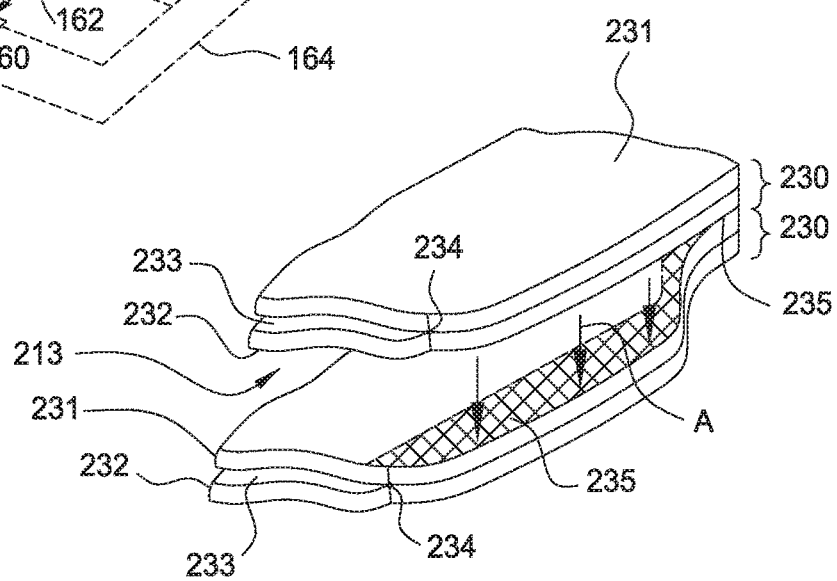
FIG. 2B is a close-up partial exploded view of a portion of the thermal exchange unit according to one embodiment of the invention.

In one embodiment, as shown in FIG. 2B, the thermal exchange unit 220 is formed by bonding or sealing two layers (e.g., layers 231 and 232) of a collapsible and pliant material together to form a composite element 230 having a fluid plenum 233 formed between the bonded and sealed layers to allow a heat exchanging fluid to be delivered from the fluid source 161 there through. FIG. 2B is a partially exploded cross-sectional view of a portion of the thermal exchange unit 220 according to an embodiment of the invention. The layers 231 and 232 can be sealed (e.g., seal 234) by use of a heat sealing, gluing, or other conventional compliant layer bonding technique. Then two or more composite elements 230 can then be bonded together (see "A" in FIG. 2B) at a sealing region 235, using a heat sealing, gluing, or other conventional technique, to form the internal region 213 in which the extremity 130 can be placed. The layers 231 and 231 may composed of a collapsible and pliant material, including but not limited to, urethane, polyurethane, polypropylenes, polystyrenes, high density polyethylene's (HDPE), low density polyethylene's (LDPE), poly (vinyl chloride), rubbers, elastomers, polymeric materials, composite materials, among others.

In one embodiment, a plurality of dimples 240 are formed between the layers 231 and 231 to form a stronger composite elements 230 that will not dramatically expand when a heat exchanging fluid is delivered from the fluid source 161 to the thermal exchange unit 220. In one embodiment, a separating feature 236 is formed through a region of the composite element 230 to allow fluid delivered from the fluid supply line 224 to flow through the fluid plenum 233 and around the separating feature 236 before the fluid exits the thermal exchanging unit 220 and enters the fluid return line 222. The separating feature 236 may be formed by RF welding, thermal sealing, gluing, or bonding the layers 231 and 231 together. In one embodiment, a composite element 230 is formed on either side, or wraps around, the extremity 130 in the device 200 to provide improved thermal contact and heat exchanging properties.

Figure 3D:
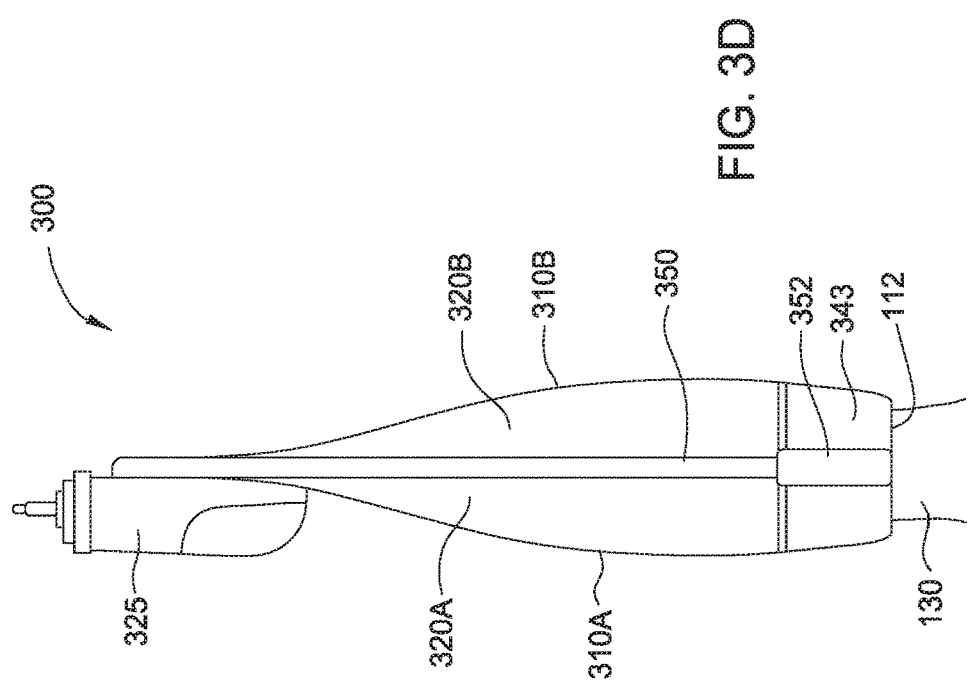
FIG. 3D is a side view of the exemplary device of FIG. 3A.
Figure 3C:
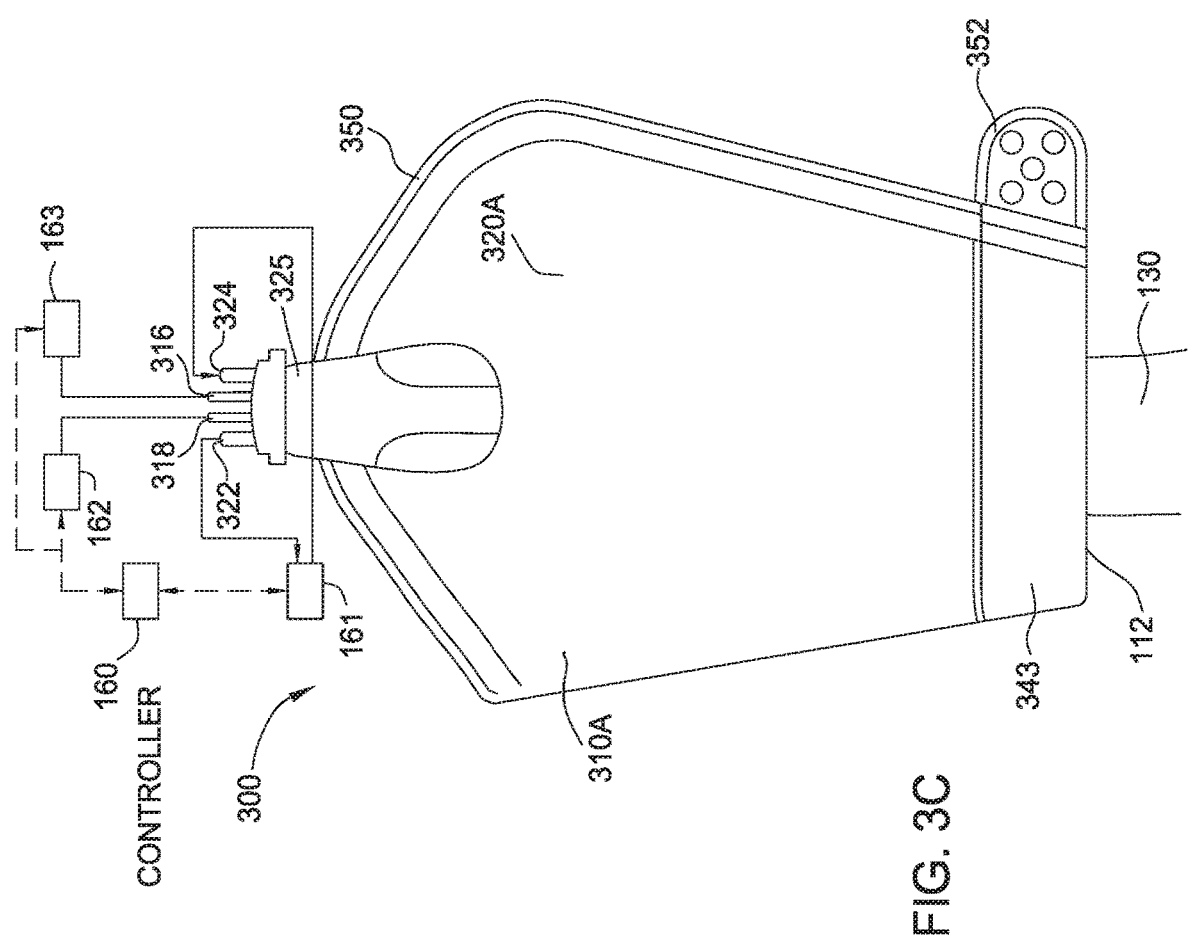
FIG. 3C is a top view of the exemplary device of FIG. 3A which is folded and enclosed according to one embodiment of the invention.

FIG. 3A is a perspective view of a device 300 in its opened and unfolded position according to one embodiment of the invention. FIGS. 3B, 3C, 3D illustrate a perspective view, a top view, and a side view of the device 300 which is folded and enclosed according to one embodiment of the invention. The device 300 may include a singular body element being flat and unfolded. Alternatively, the device 300 may include a first body element 310A and a second body element 310B, as shown in FIG. 3A. The first body element 310A and the second body element 310B can be folded, for example, through the direction of an arrow A, to form the opening 112 (FIG. 3B) and to enclose a portion of the extremity 130 of a mammal.

The first body element 310A and the second body element 310B may be comprised of the same material as the body element 110 of the device 100. The size of the opening 112 may be sealed and reduced by a sealing element 342. The material of the sealing element 342 may be the same material as the sealing element 140 discussed above. In addition, the device 300 generally further includes one or more thermal exchange units 320A and 320B capable of containing a thermal-exchange fluid medium therein. Optionally, the first body element 310A and the second body element 310B may be connected to the opening 112 through a body element 343. Alternatively, the body of the first body element 310A and the second body element 310B can directly form the opening 112 without the use of an additional body element 343. In one embodiment, the first body element 310A, the second body element 310B, and the additional body element 343 are formed from a collapsible and pliant material, including but not limited to, urethane, polyurethane, polypropylenes, polystyrenes, high density polyethylene's (HDPE), low density polyethylene's (LDPE), poly(vinyl chloride), rubbers, elastomers, polymeric materials, composite materials, among others.

In operation the device 300 is folded so that the edges 350 of the first body element 310A and the second body element 310B may be enclosed by an enclosing clip 352, for example, through the direction of an arrow B (FIG. 3B), such that the opening 112 is formed for the portion of the extremity to be inserted therein. The mechanism by which the enclosing clips 352 can be used to enclose the edges 350 of the first body element 310A and the second body element 310B may vary and include fasteners, zippers, snaps, buttons, hydrogel coated tabs, conventional tape type materials, hook/loop type systems, among others. For example, the edges 350 of the first body element 310A and the second body element 310B may be reinforced such that the edges 350 can stayed together via the enclosing clip 352 and hold the portion of the extremity 130 in place until vacuum or reduce pressure is applied to the internal region 313 formed between the first body element 310A and the second body element 310B.

Further, a generalized port 325 can be used to bundle up the various fluid ports and pressure ports together. The generalized port 325 can be used to fluidly or electrically connect the controller 160 (see FIG. 3C), the fluid source 161, vacuum sensor 162, and/or a pump 163 to the various components found in the internal region 313 of the device 300. For example, the generalized port 325 may include a pressure port 316, a pressure sensing line 318, a fluid supply line 324, and a fluid return line 322 therein. The generalized port 325 may also be used to connect to one or more compression air plenums for applying a compression pressure on the portion of the extremity 130.

Figure 4A:
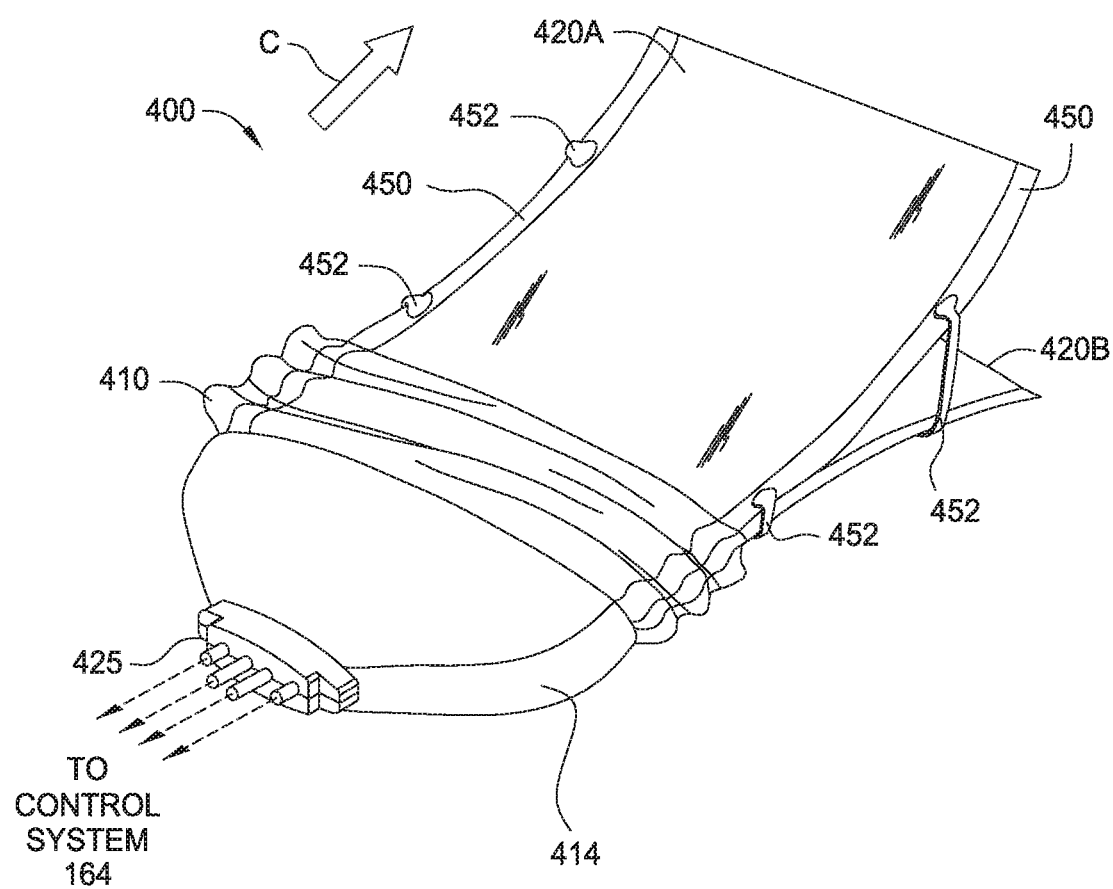
FIG. 4A is an exemplary device which is to be enclosed before a portion of an extremity is disposed according to one embodiment of the invention.
Figure 4B:
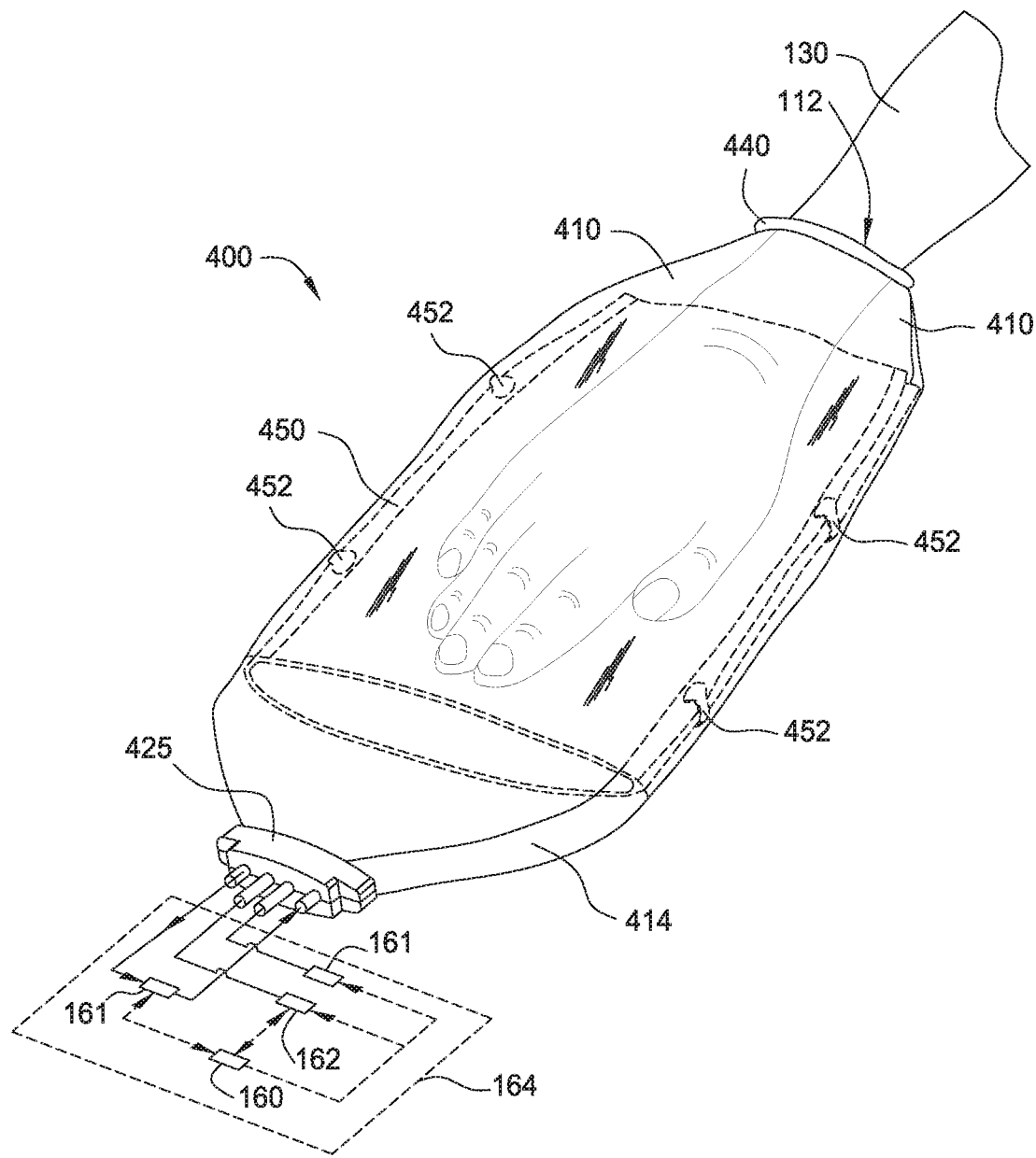
FIG. 4B is another exemplary device which is enclosed with a portion of an extremity disposed therein according to one embodiment of the invention.

FIG. 4A is another example of a device 400 according to one embodiment of the invention that is in an "open" position to receive an extremity 130 (See FIG. 4B). FIG. 4B illustrates the device 400 which is configured to enclose a portion of the extremity 130 disposed therein according to one embodiment of the invention. The device 400 includes a body element 410 which can be folded and/or rolled up and down to form the opening 112 to enclose a portion of the extremity 130 of a mammal. The body element 410 may be comprised of the same material as the body element 110 of the device 100. In addition, the device 400 may further include one or more thermal exchange units 420A and 420B capable of containing a thermal-exchange fluid medium therein.

Referring to FIG. 4B, the size of the opening 112 formed when the extremity 130 is enclosed within the device 400, may be sealed by use of a sealing element 440. The material of the sealing element may be the same material as the sealing element 140.

In operation, the device 400 is unfolded and folded according to the direction of an arrow C to cover and enclose the thermal exchange units 420A and 420B and the extremity 130. FIG. 4B illustrates the device 400 in an enclosed configuration. In one embodiment, during the process of enclosing the extremity 130, the edges 450 of the thermal exchange units 420A and 420B may be urged together by one or more enclosing clip 452 and the opening 112 can be formed for the portion of the extremity 130 to be inserted therein. The mechanism by which the enclosing clips 452 can be used to enclose the edges 450 may vary and include fasteners, zippers, snaps, hydrogel coated tabs, conventional tapes, buttons, and hook/loop type systems, among others. For example, the edges 450 of the thermal exchange units 420A and 420B may be reinforced such that the edges 450 can be sealed and snapped-locked tightly by the enclosing clips 452. Further, a generalized port 425 can be used to bundle up the various fluid lines and pressure lines together that are connected to the controller 160, the fluid source 161, vacuum sensor 162 an/or a pump 163 (FIG. 4B). In addition, a manifold 414 may be used to help connect and disconnect the various fluid ports and pressure ports between the generalized port 425 and the thermal exchange units 420A and 420B.

Figure 4C:
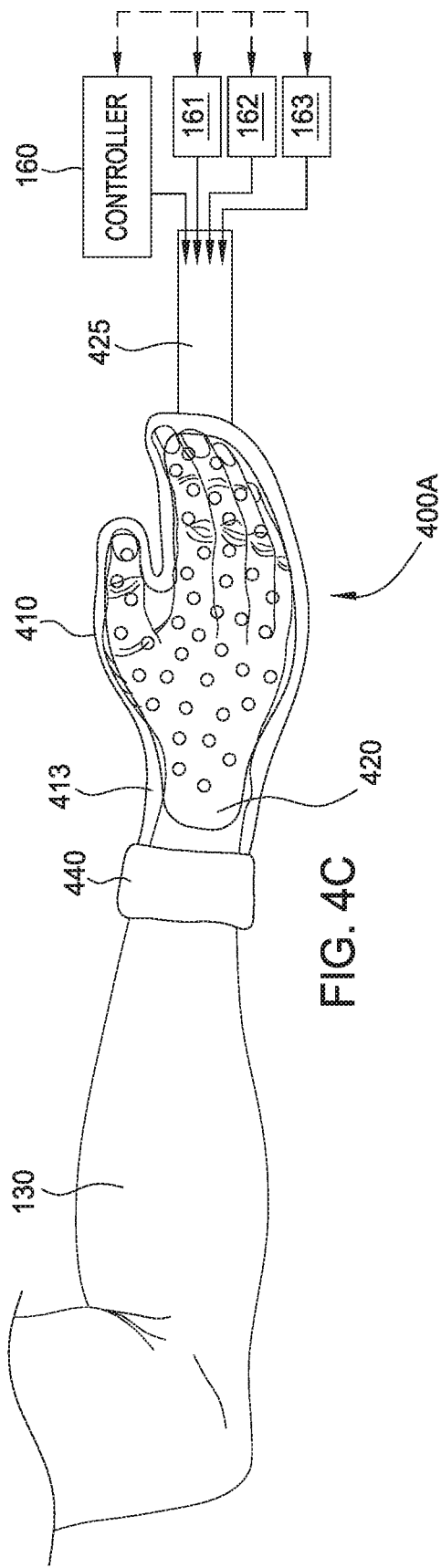
FIG. 4C is another exemplary device with a portion of an extremity disposed and sealed therein according to one embodiment of the invention.
Figure 4D:
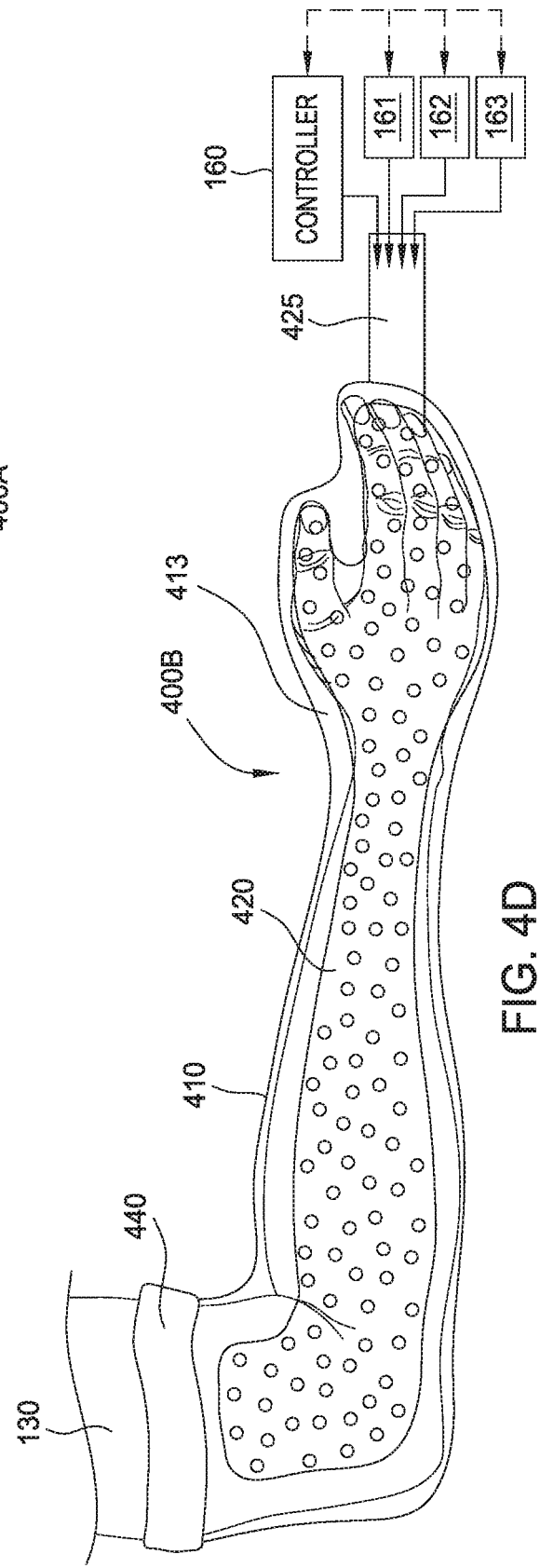
FIG. 4D is another exemplary device with a large portion of an extremity disposed and sealed therein according to one embodiment of the invention.

FIGS. 4C and 4D illustrate examples of the device 400, such as device 400A (FIG. 4C) and device 400B (FIG. 4D), with a portion of an extremity 130 disposed and sealed therein according to one or more embodiments of the invention. The extremity 130 to be enclosed by the device 400A can be a hand, as shown in FIG. 4C, in which the device 400A is shaped like a mitten or a glove. In this configuration, the one or more thermal exchange units 420 are sized to heat the desired area of the extremity 130 that is positioned within the body element 410. The internal region 413 of the device 400A can be evacuated and the thermal exchange unit(s) 420 can be temperature regulated by use of the controller 160, fluid source 161, vacuum sensor 162 an/or a pump 163, which is schematically illustrated in FIG. 4C. While only a single thermal exchange unit 420 is shown n FIGS. 4C and 4D, this configuration is not intended to be limiting to the scope of the invention, and thus two or more thermal exchange units 420 may be positioned around various parts of the extremity 130 to improve perfusion.

As shown in FIG. 4C, alternatively, the extremity 130 enclosed in the device may be a large portion of an arm, or other appendage. The device 400B can be shaped like an elongated glove to conformably enclose the arm. The increased surface area of the body enclosed and temperature controlled by use of the thermal exchange unit(s) 420 shown in FIG. 4D versus FIG. 4C may be useful to help more rapidly and/or easily control the subjects body temperature during use.

Referring to FIGS. 4C and 4D, a generalized port 425 can be used to bundle up various fluid ports and pressure ports together and connected to the controller 160, the fluid source 161, vacuum sensor 162 an/or a pump 163.

Figure 5A:
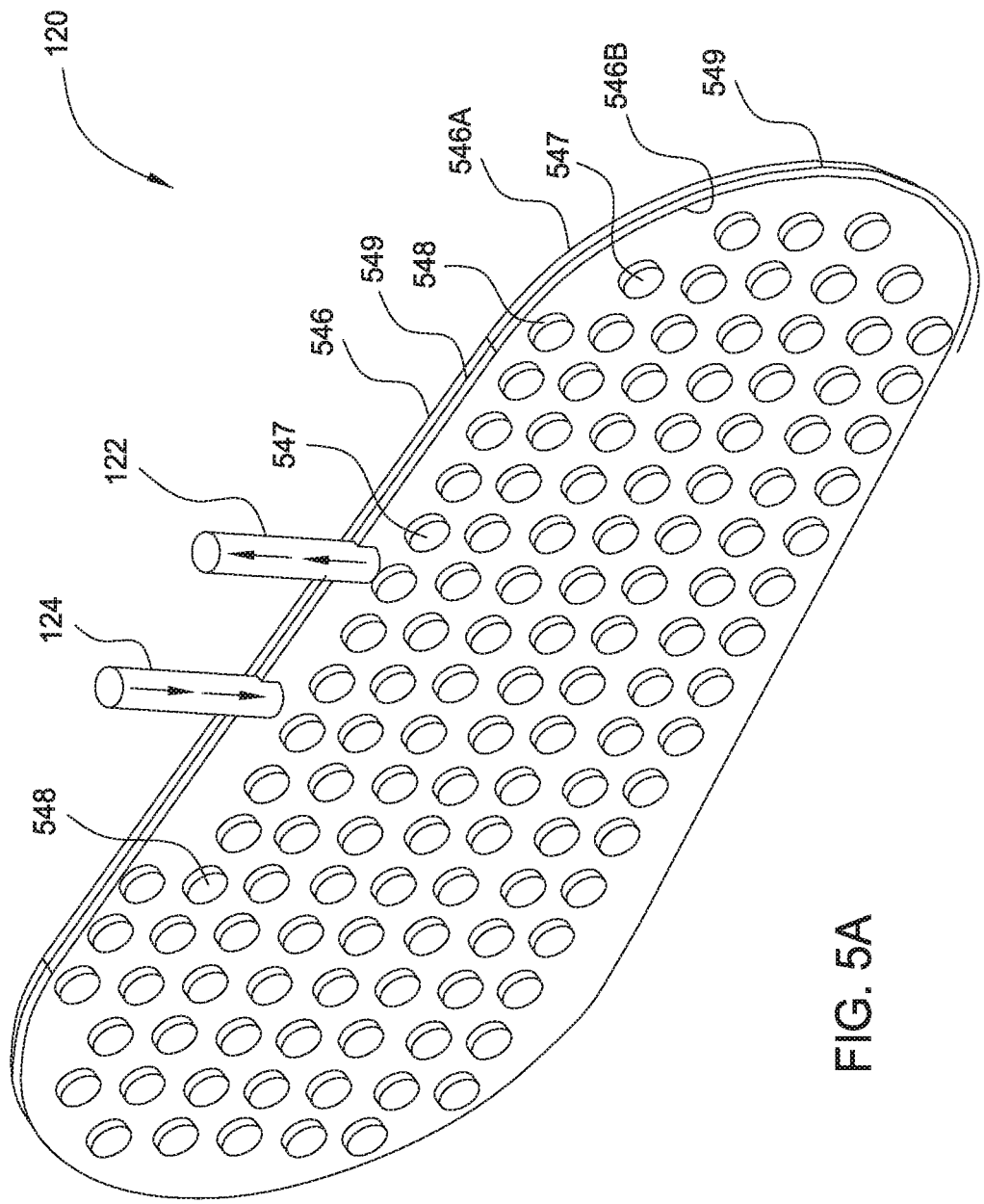
FIG. 5A illustrates one example of a thermal exchange unit according to one embodiment of the invention.

FIG. 5A illustrates one example of the thermal exchange unit 120, such as the thermal exchange units 120A, 120B, 220, 320A, 320B, and 420 discussed herein, according to one embodiment of the invention. The thermal exchange unit 120 includes a thermal exchange body 546 having sides 546A and 546B. One side (e.g., side 546B) of the thermal exchange body 546 includes a plurality of thermal contact domes 548 that have a thermal contact surface 547 that can be applied to a portion of the extremity 130. The diameter of the thermal contact surfaces 547 and the shapes or sizes thereof can vary such that the sum of the total area of the thermal contact surfaces 547 can be maximized. The thermal exchange unit 120 may further include the thermal fluid supply line 124 and the thermal fluid return line 122 connected to a thermal fluid source (e.g., fluid source 161 FIG. 1A) for circulating a thermal fluid medium through the thermal exchange body 546 of the thermal exchange unit 120.

The material of the thermal exchange body 546 may be any flexible, conductive and/or durable material, for example, any of the materials suitable for the body element 110. In one embodiment, the thermal exchange body 546 is made of a flexible material which can easily conform to the shape of the extremity 130. In another embodiment, the thermal contact domes 548 are made of a rigid material to provide rigid contacts to the extremity 130.

In addition, the material of the thermal contact domes 548 may be a material which provides high thermal conductivity, preferably much higher thermal conductivity than the material of the thermal exchange body 546. For example, the thermal contact domes 548 may be made of aluminum, which provides at least 400 times higher thermal conductivity than plastics or rubber materials. In one embodiment, the thermal exchange unit 120 can be formed and assembled through RF welding. In another embodiment, the thermal exchange unit 120 may be formed and assembled through injection molding. There are many possible ways to design and manufacture the thermal exchange body 546 to provide a flexible thermal exchange unit that does not leak. In one embodiment, the thermal exchange unit 546 is formed by bonding a compliant material that is sealed using conventional techniques at a joint 549.

In one embodiment, the thermal exchange unit is formed from layers of several materials bonded together to form internal fluid flow paths for thermal fluids to be delivered therein. The multiple layer configuration may result in uneven surfaces, due to the presence of the internal fluid flow paths. The resulting bumpy surfaces may provide less contact, thereby reducing surface area needed for maximum thermal transfer. The thermal exchange body 546 may also be formed using a low thermal conductivity material, such as polyurethane. To prevent these problems from affecting the results, the thermal exchange body 546 may be covered by one or more backing sheets such that a flat and even contact is made to the extremity. In addition, the backing sheet can be made of high thermal conductive material to provide high thermal conductivity between the thermal exchange unit 120 and the extremity. For example, the backing sheets may be made of a thin metal sheet, such as aluminum (like a foil) or other metal sheets. In general, aluminum or other metal materials may provide higher thermal conductivity than plastics or rubber, e.g., at least 400 times higher.

Figure 5B:
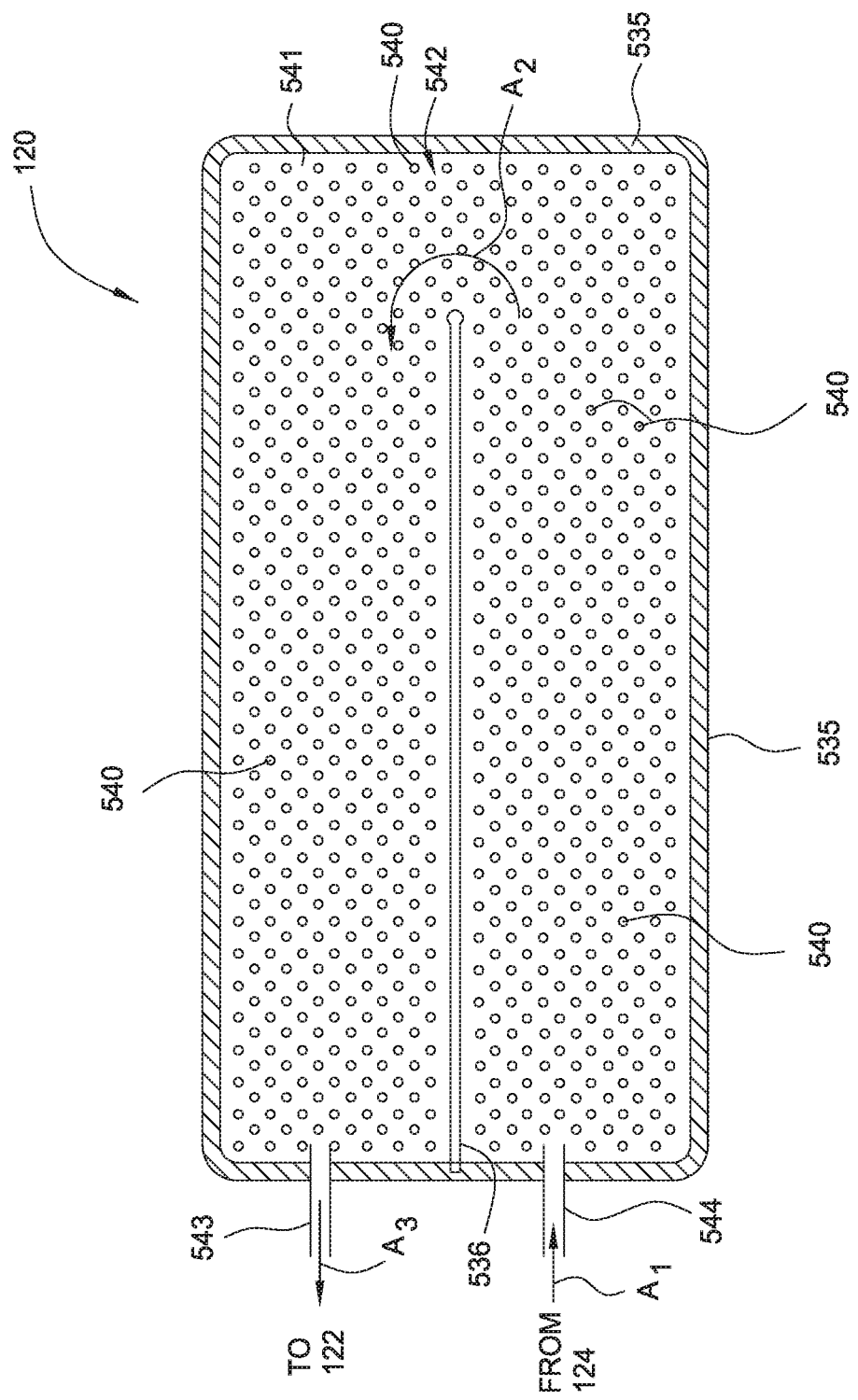
FIG. 5B illustrates one example of a thermal exchange unit according to one embodiment of the invention.

FIG. 5B illustrates another embodiment of the thermal exchange unit 120 that is formed using two layers of a compliant material 541 that are sealed at the edge region 535 by use of an RF welding, thermal sealing, gluing or other bonding process to form a sealed main body 542. The main body 542 may have an inlet port 544 and an outlet port 543 that are in fluid communication with the fluid source 161, and the fluid supply line 124 and fluid return line 122, respectively. The region formed between the two layers of the compliant material 541 is thus used as a fluid plenum that can receive (see arrow $A_1$) and then exhaust (see arrow $A_3$) the thermal fluid medium from the fluid source 161. In one embodiment, a separating feature 536 is formed in the thermal exchange unit to separate the fluid delivered into the inlet port 544 and the outlet port 543, and thus allow the thermal exchanging fluid to follow a desirable path through fluid plenum to optimize and/or improve efficiency of the heat transfer process. In one example, the fluid flow path sequentially follows the arrows $A_1$, $A_2$ and $A_3$. The separating feature 536 can be formed in the sealed main body 542 by RF welding, thermal sealing, gluing or other bonding process to bond the two layers of the compliant material 541 together. In one embodiment, a plurality of dimples 540 are formed between the layers of compliant material 541 in the sealed main body 542 by RF welding, thermal sealing, gluing or other bonding process to form a structure that will not expand when a heat exchanging fluid is delivered to the internal region of the sealed main body 542. In one embodiment, the thermal exchange unit 120 is formed and assembled through RF welding or thermal sealing techniques. In another embodiment, the thermal exchange unit 120 may be formed and assembled through injection molding. In one embodiment, the thermal exchange unit 120 illustrated in FIG. 5B is formed from a pliant material, including but not limited to, urethane, polyurethane, polypropylenes, polystyrenes, high density polyethylene's (HDPE), low density polyethylene's (LDPE), poly(vinyl chloride), rubbers, elastomers, polymeric materials, composite materials, among others.

Alternatively, one or more thermal exchange units 120 may be an electric pad having one or more electric wires connected to a power source. For example, the power source may be a low voltage DC current power source. In addition, the one or more thermal exchange units may include a thermocouple to monitor the temperature and a thermo switch to automatically shut off the electric power when the temperature of the electric pad passes a safety level.

The thermal exchange units as described herein (e.g., reference numerals 120, 120A, 120B, 220, 320A, 320B, and 420) according to embodiments of the invention generally provide thermal exchange surfaces, with increased surface area, to heat, cool, and/or regulate the temperature of an extremity of a mammal. The thermal exchange units can be used to regulate the blood flow in an appendage by a variety of means. For instance, applying a temperature to a hand of about 0° C. to 10° C. can cause an increase in the average blood flow due to a phenomenon called the "hunting response" which keeps hunters and fisherman from getting frostbite while working in the extreme cold with their bare hands. Different individuals respond differently to cold applied to the hands, and in a some well known laboratory tests, application of cold to the hands of a person from the Indian sub-continent improved average blood flow, but not as much as the same treatment improved the average blood flow in the typical Eskimo.

In some cases, the perception of warmth is enough to improve blood flow. For instance, a 23° C. (room temperature) water pad feels cool in intimate contact with the leg of a normothermic subject who otherwise feels warm, and the "COOLNESS" of the pad can measurably reduce blood flow in the leg. However, if the same person's leg has been exposed to 5° C. cold for prolonged periods, this same 23° C. (room temperature) water pad feels warm in comparison, so that it can actually increase blood flow in the same leg. Therefore the temperature blood flow relationship is determined by both perceived warmth and applied temperature. The application of the heat above the core body temperature is also able to increase blood flow.

It is noted that one or more thermal exchange units individually or in combination, can be positioned and attached to one or more portions of the body element of the invention to provide thermal exchange and regulate the temperature of a mammal's extremity provided inside the devices as described herein. In one embodiment, one or more thermal exchange units can be pre-assembled inside the devices. In another embodiment, one or more thermal exchange units can be assembled into the devices prior to use.

Figure 6A:
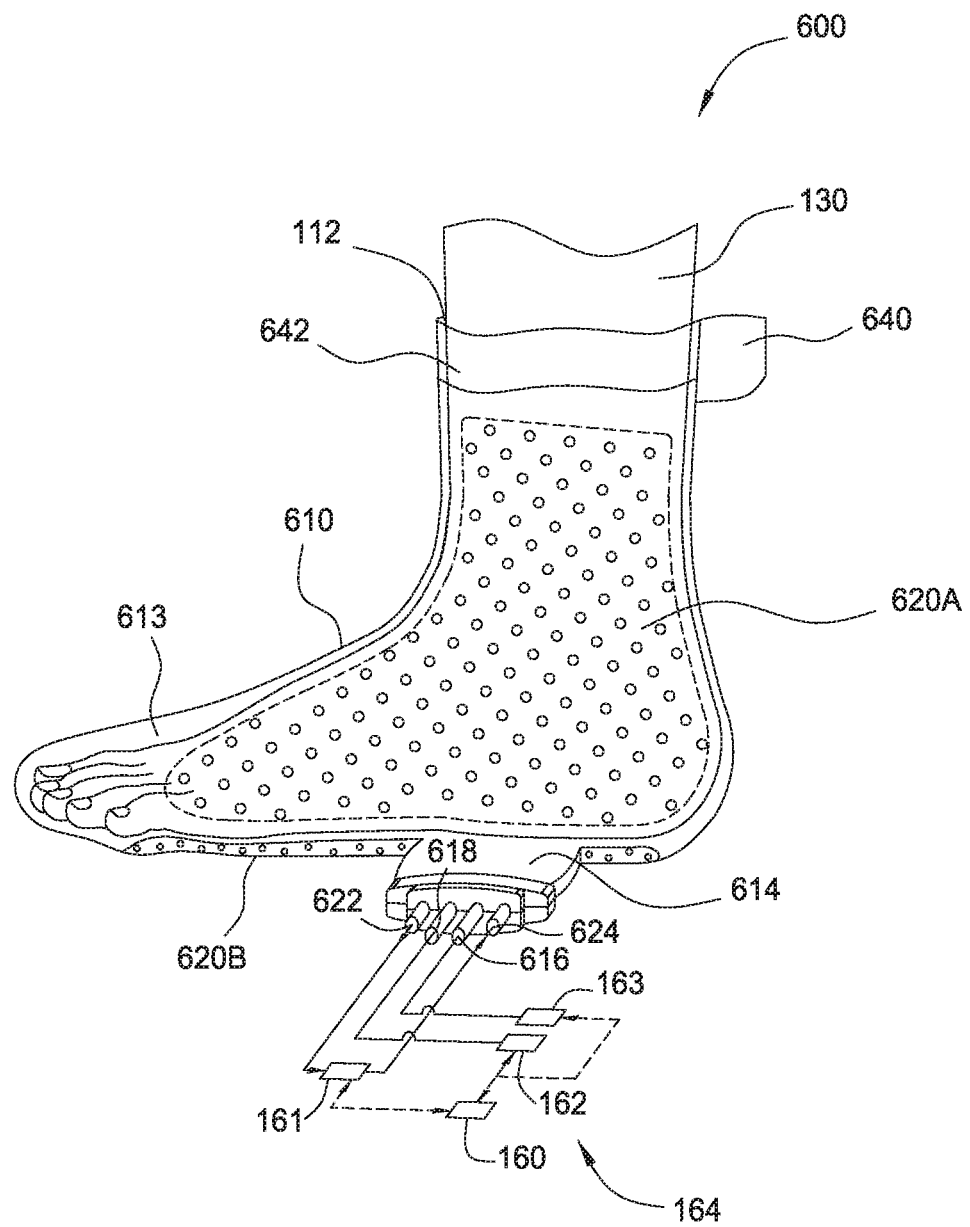
FIG. 6A is a side view of an exemplary lower extremity device according to one embodiment of the invention.

FIG. 6A is a side view of one example of a device 600, which may be used increase blood flow and control the temperature of a lower extremity of a mammal, such as a foot, according to one embodiment of the invention. The device 600 includes a body element 610 for forming a pressurized volume, one or more thermal exchange units 620A, 620B positioned on various sides/portions of the extremity 130, the opening 112 for containing the extremity 130, and a sealing element 640 attached to the opening 112. An additional sealing element, such as a sealing element 642, may be used to adequately seal the extremity 130 within an internal region 613 of the device 600.

The body element 610 is generally be flat or occupying a minimized space or volume such that the device 600 can easily and conveniently be folded, stored, or shipped. The body element 610 is capable of expanding from the minimized volume into an expanded space or volume for containing a portion of an extremity of a mammal therein. Under a pressurized condition, the volume or space of the body element 610 is reduced from the expanded volume into a pressurized volume, such as a volume to conformably enclose the portion of the extremity 130. As a result, the pressure applied to the extremity 130 enclosed inside the internal region 613 of the device 600 is distributed evenly and equally. The minimized volume and the expanded volume can be maintained under atmospheric pressure.

The body element 610 may be comprised of the same collapsible and pliant material as the body element 110, such as a transparent or semi-transparent material that allows viewing of the extremity 130 positioned therein. The thickness of the collapsible and pliant material is not limited as long as it can sustain the pressurized conditions when the device 600 is used; for example, a thickness of from about 0.5 mils to about 20 mils, such as about 1.5 mils to about 12 mils, can be used to pliantly conform to the shape and size of the portion of the extremity 130 contained therein. Accordingly, the materials of the body element 610 and the thermal exchange units 620A, 620B are made of a flexible material, which can be pliant and easily collapsible to conform into the shape of the extremity 130 and securely surround and enclose the portion of the extremity 130. The material for the thermal exchange units 620A, 620B and the body element 610 are generally comprised of collapsible and pliant material similarly discussed above in conjunction with thermal exchange units (e.g., reference numerals 120, 120A, 120B) and body element 110. The materials used in the thermal exchange units 620A, 620B and/or the body element 610 are generally selected to allow good contact between the surfaces of the extremity 130 and the thermal exchange units 620A, 620B and/or the body element 610 when a subatmospheric pressure or a vacuum pressure level is achieved within the internal region 613 of the device 600.

The one or more thermal exchange units 620A, 620B, etc., are attached to one or more portions of the body element 610 and adapted to contact a portion of the extremity 130 that is under the pressurized condition, and to increase, reduce, or maintain the temperature of the extremity 130 received therein. The thermal exchange unit 620A, 620B can be permanently or detachably placed inside the device 600 to provide thermal exchange for the extremity 130 received therein. In one example, the thermal exchange units discussed in conjunction with FIG. 5A or 5B can be adapted to meet the configuration requirements of the thermal exchange units 620A, 620B shown in FIGS. 6A-6C. Alternatively, the thermal exchange unit may include an electric pad, as described in detail in co-pending U.S. provisional patent application Ser. No. 60/821,201, filed Aug. 2, 2006, which is incorporated by reference herein.

The body element 610 may include one or more apertures for attaching various fluid ports or pressure ports, such as a pressure port 616, a pressure sensing port 618, the fluid supply line 624, and the fluid return line 622, among others. Accordingly, one or more thermal exchange supply lines and one or more thermal exchange return lines can be connected to one or more thermal sources through the one or more apertures on the body element 110. As shown in FIG. 6A, one or more tubing's, lines, and ports can be bundled together and connected to a manifold 614 to allow the fluid sources 161, pumps 163, vacuum sensor 162 and/or a controller 160 to be easily connected for easy transportation and operation. In one embodiment, the manifold 614, as shown in FIG. 7, incorporates quick-connecting and quick-disconnecting fittings, similar to CPC Colder Products Company in St, Paul, Minn. In addition, the manifold 614 may be formed on a portion of the body element 610 for connecting the various fluid ports or pressure ports to pass through the one or more apertures of the body element 610 to other vacuum manifold, fluid sources outside of the device 600 through various kinds of tubing's and/or manifold connectors. The manifold 614 may be connected to the one or more apertures of the body element 610, the one or more pressure ports and the one or more thermal exchange units of the device 600. The position of the apertures for the fluid ports or pressure ports can be located near any convenient portions of the body element 610 and can be close to the manifold 614 or grouped together for passing through the body element 610 via a single aperture. FIG. 6D illustrates another configuration of the device 600 in which the manifold 614 is attached to a desired region of the body element 610 to provide a central place where connections can be made to the internal and external components in the device 600.

The sealing element 640 is formed on a portion of the opening 112 and adapted to seal the portion of the extremity 130 when placed inside the pressurized volume of the body element 610 so that a pressurized condition can be applied to the mammal's extremity. The sealing element 640 may be made of the same material as the sealing element 140 (FIG. 1A) and can be attached or detachably attached to the opening 112. In addition, the sealing element can be used for contacting with the skin of a mammal and capable of producing an airtight seal. The pressurized volume defined by the body element 610 and the sealing element 640 of the device 600 is created by applying vacuum or negative pressure to the pressure port 616, which can be adapted to be connected to a pump 163 (FIG. 6A) to reduce the pressure of the internal region 613. In addition, the pressure level inside the chamber or the pressurized, reduced volume enclosed by the body element 610 can be monitored by a vacuum sensor 162 placed inside the pressurized volume or space attached to the pressure sensing port 618. One or more pressure ports may be adapted to be connected to at least one pump 163 on one end and the body element 610 on the other end.

According to an embodiment of the invention, the device 600 can be used in combination with a mechanical compression device or a pressurized compression device. Alternatively, the device can itself be modified to include one or more pressure-applying gas plenums in order to apply pressurized compression forces, or a positive gas pressure to an extremity of a mammal (e.g., in the internal region 613), while also applying a thermal controlled fluid medium to a fluid exchange unit contacting the extremity and/or applying vacuum or negative pressure to a portion of the extremity.

Figure 6B:
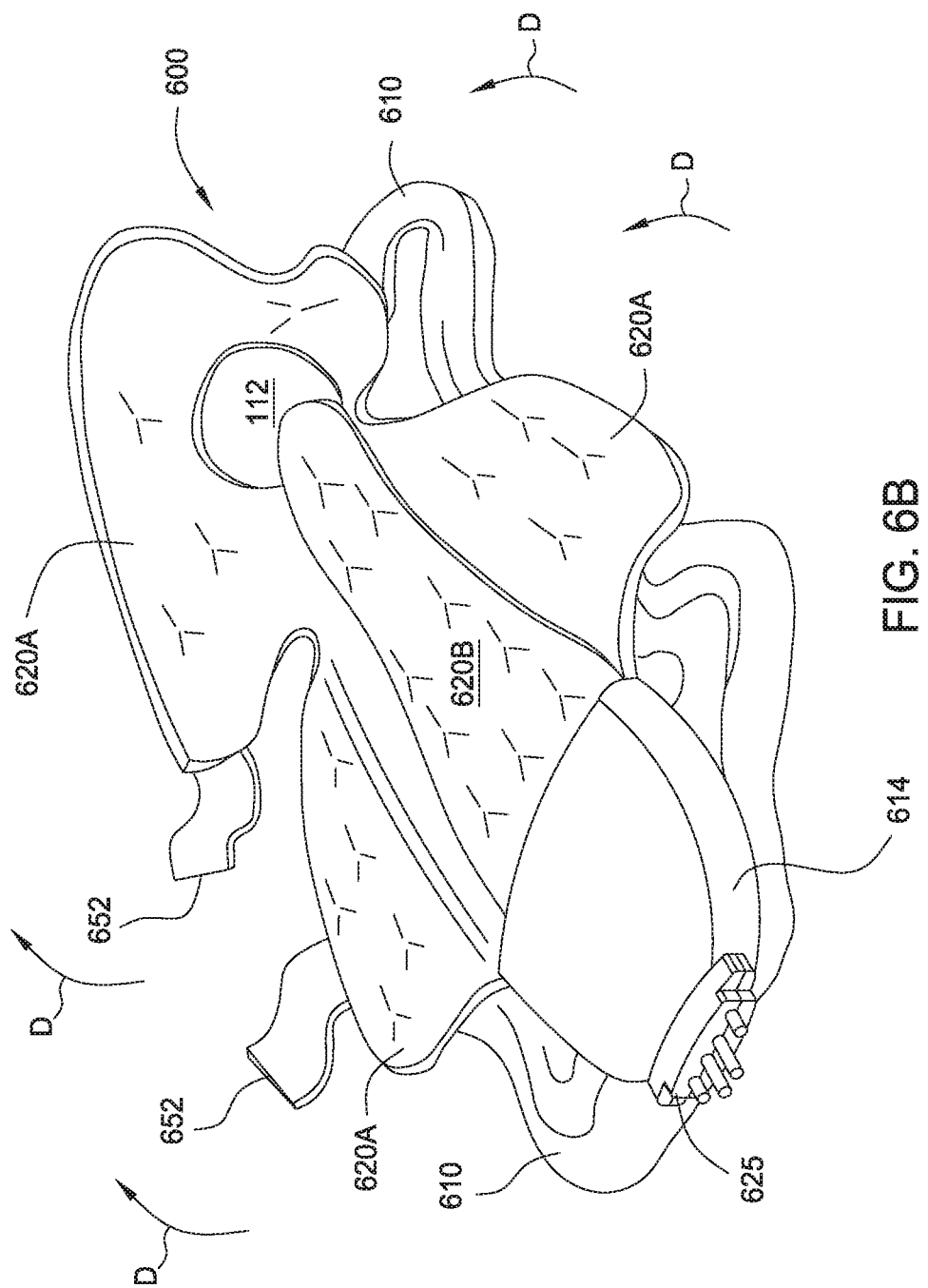
FIG. 6B is a perspective view of an exemplary lower extremity device which is not yet folded nor enclosed according to one embodiment of the invention.
Figure 6C:
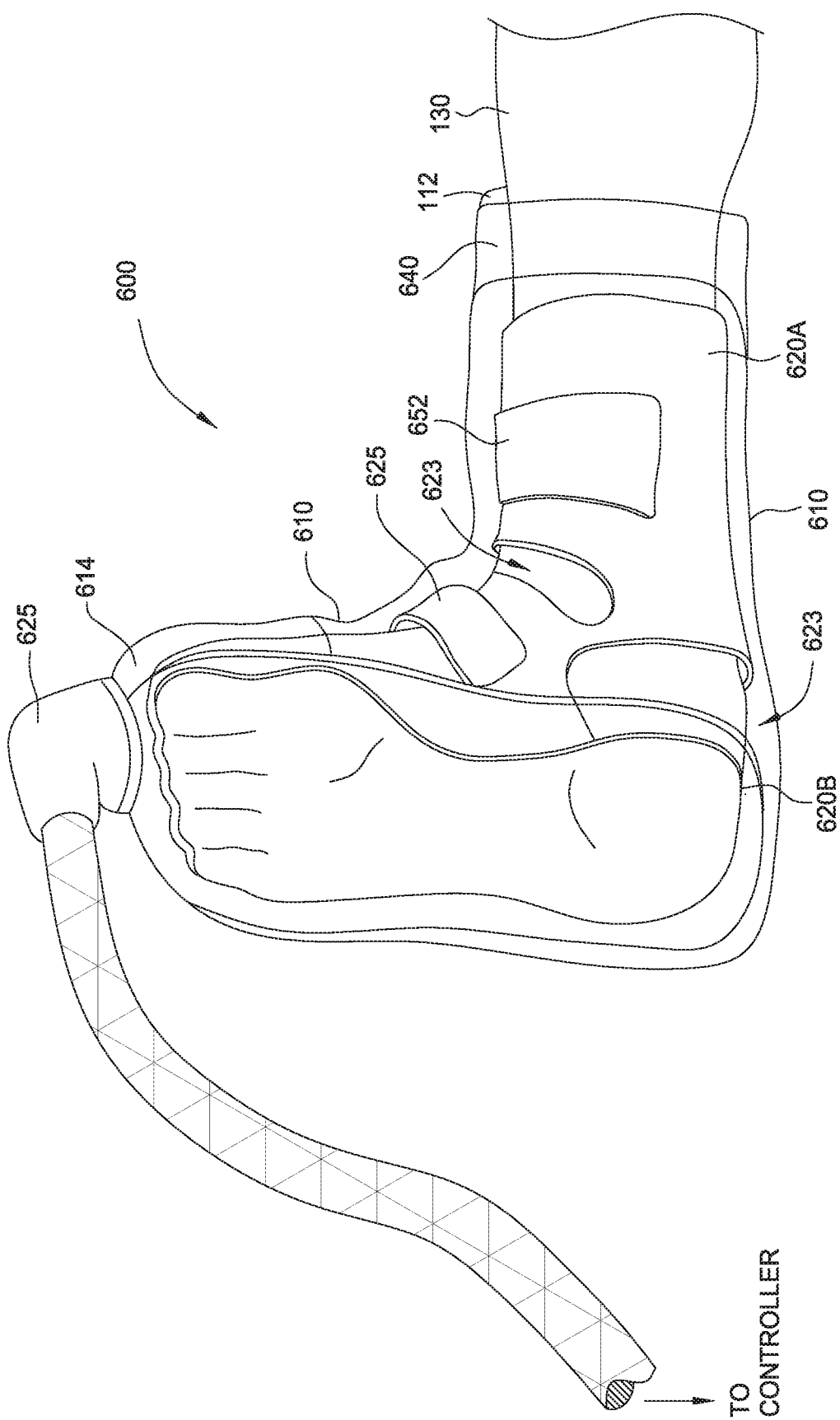
FIG. 6C is a perspective view of an exemplary lower extremity device which is folded, enclosed and sealed according to one embodiment of the invention.
Figure 6D:
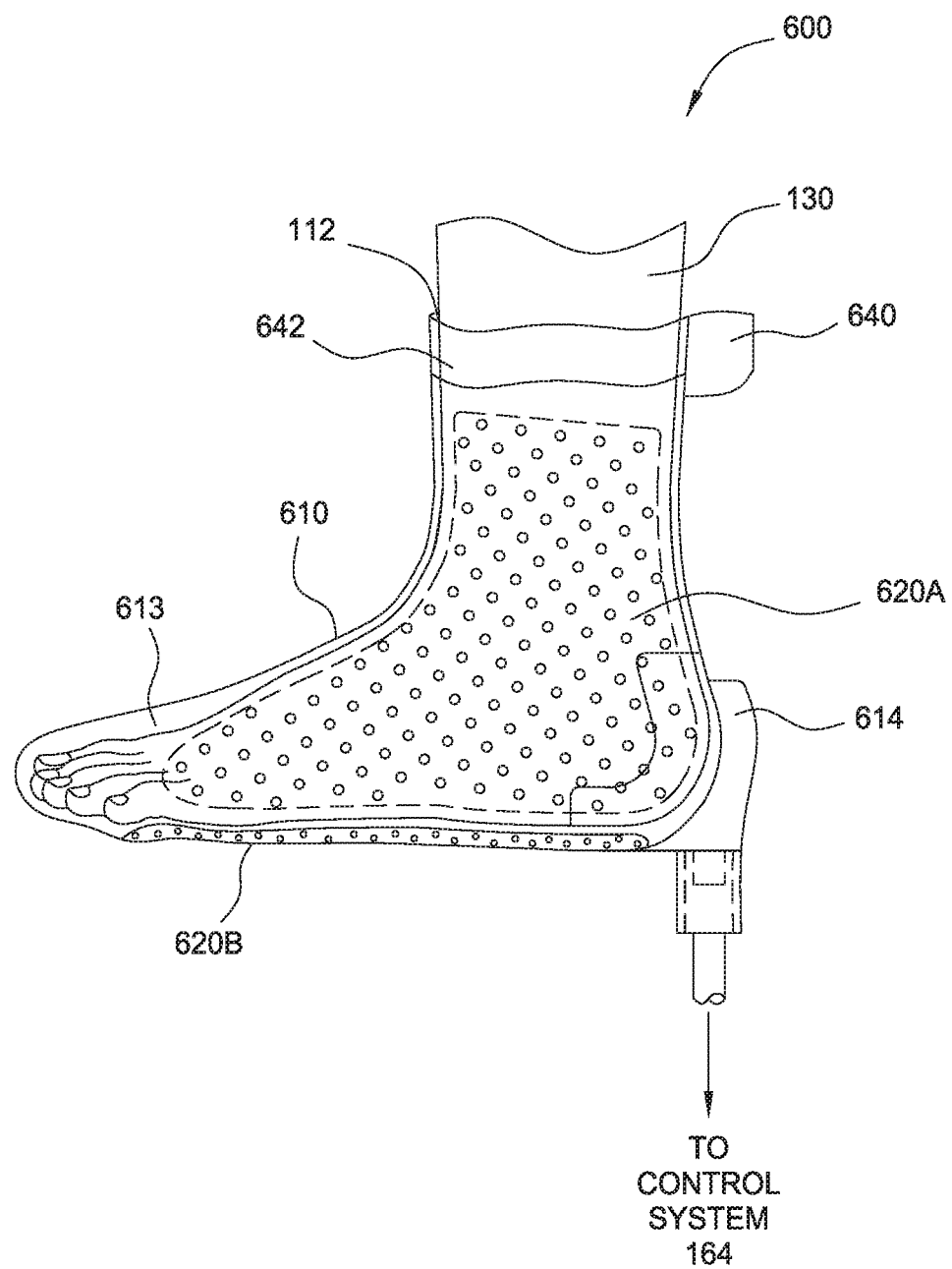
FIG. 6D is a side view of an exemplary lower extremity device according to one embodiment of the invention.

FIG. 6B is a perspective view of an exemplary lower extremity device which is not yet folded nor enclosed by the body element 610. FIG. 6C is a perspective view of an exemplary lower extremity device which is folded, enclosed and sealed according to one or more embodiments of the invention. The device 600 may include a singular body element 610 capable of laying flat, rolled and/or unfolded, as shown in FIG. 6B. Alternatively, the device 600 may include more than one body elements 610.

In addition, the device 600 further includes one or more thermal exchange units 620A and 620B capable of containing a thermal-exchange fluid medium therein. The body element 610 and the thermal exchange units 620A, 620B can be folded, for example, through the direction of arrows D, to enclose a portion of the extremity 130 of a mammal. In operation the device 600 is folded by securing the positions of the thermal exchange units 620A, 620B and adjusting accordingly to the size of the extremity 130. The thermal exchange units 620A, 620B and the body element 610 can be properly folded, secured, and/or adjusted through one or more enclosing clips 652 located on one or more positions on the thermal exchange units 620A, 620B and the body element 610. The one or more enclosing clips 652 can be, for example, Velcro type fasteners, as shown in FIGS. 6B and 6C, or another other suitable, clips, fasteners, zippers, snaps, tabs, tongs, adhesives, Velcro fasteners, hydrogel coated tabs, conventional tapes, buttons, occlusion cuff, hook/loop type systems, etc. before or after a leg is positioned therein. Next, the body element 610 can then be positioned over the thermal exchange units 620A and 620B to form the opening 112 in which the extremity 130 is disposed. The size of the opening 112 may be sealed by the sealing element 640 (FIG. 6A).

Further, a generalized port 625 can be used to bundle up various fluid ports and pressure ports together and connected to the controller 160, the fluid source 161, vacuum sensor 162 an/or a pump 163. The one or more tubing's, lines, and ports can be bundled together and connected to the manifold 614 for connecting to thermal regulation fluid sources, vacuum pumps, and/or a controller unit (not shown) for easy transportation and easy connection. As shown in FIGS. 6B and 6C, the manifold is convenient located to near the front toe portions of a foot. FIG. 6D illustrates a convenient connection near the heal of a foot.

Referring to FIG. 6C, in one embodiment, the thermal exchange units 620A, 620B contain one or more relieved regions 623 that allow for movement of the extremity 130 during the use of the device 600. The placement of the relieved regions 623 in the thermal exchange units 620A, 620B may be strategically positioned to only allow heat transfer to desired regions of the extremity 130. It has been found that exchanging heat with certain areas of certain extremities can be unpleasurable. For example, it has been found that providing heat to the heal region of a foot can be an unpleasurable experience for some subjects, and thus, as shown in FIG. 6C, the heal region of the thermal exchange units 620A, 620B has been removed to form the relieved region 623 at the heel. In one embodiment, the heat transfer portion of the thermal exchange units 620A, 620B near the heal region is removed to remove or prevent the process from being unpleasant.

Figure 6F:
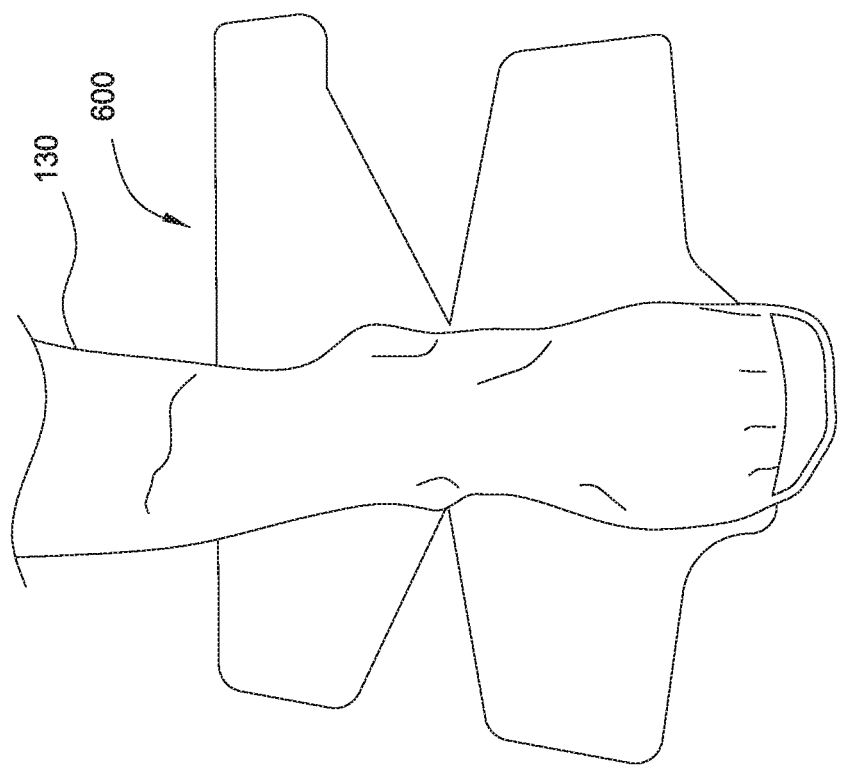
FIGS. 6E-6F are isometric views of various sized lower extremities positioned on the device illustrated in FIG. 6B according to one embodiment of the invention.
Figure 6E:
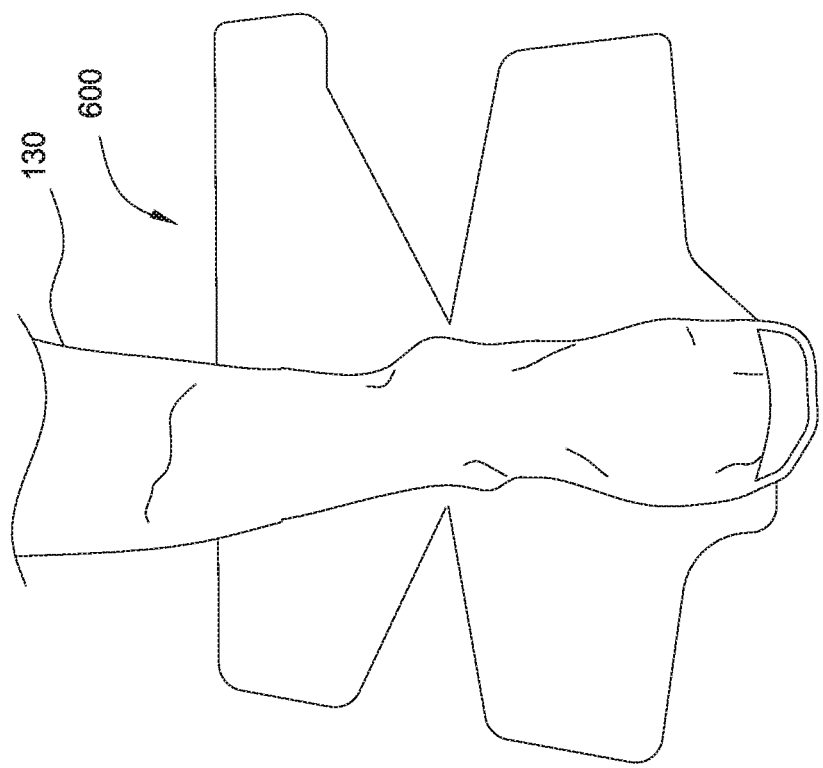
Figure 6G:
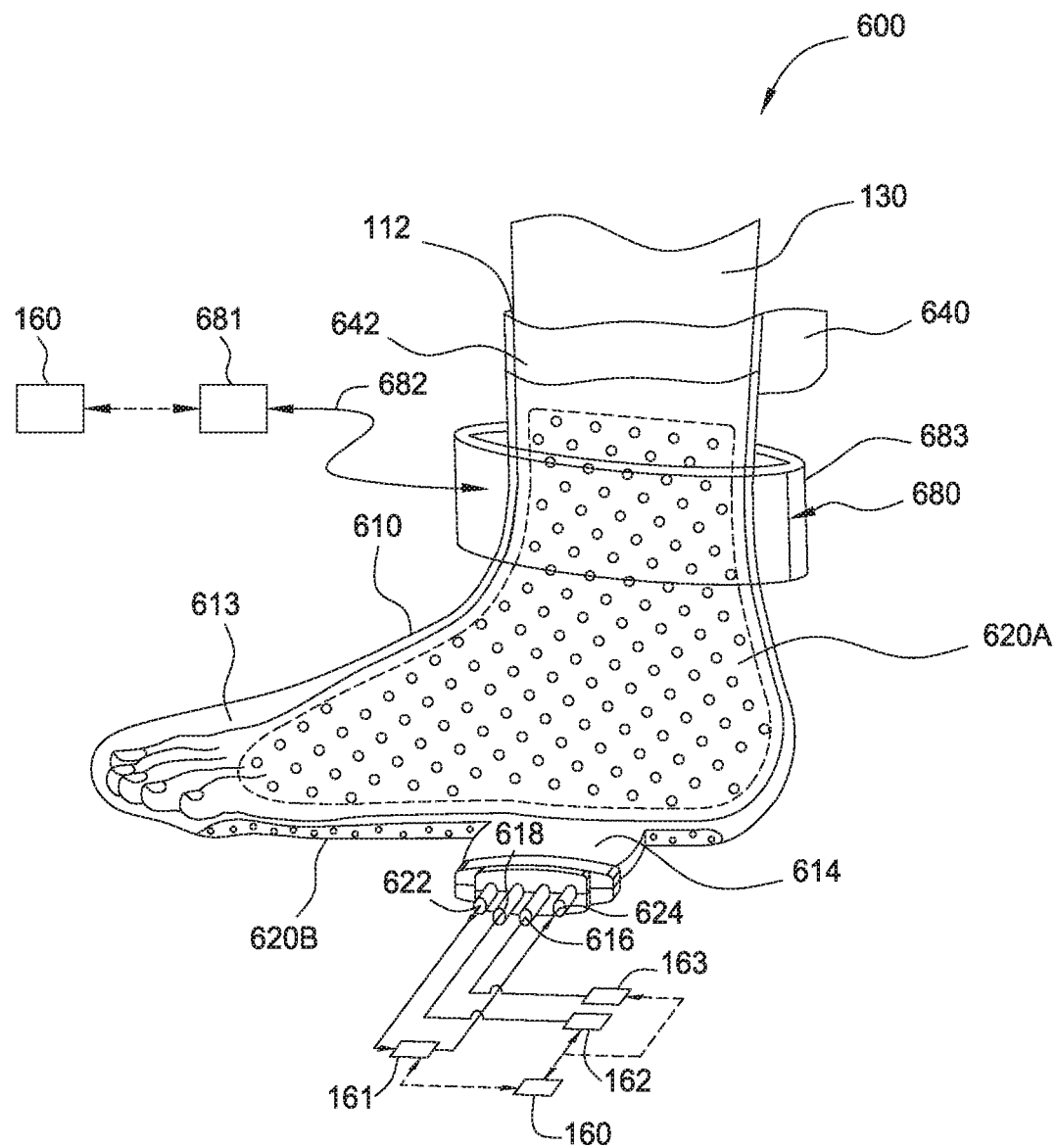
FIG. 6G is a side view of an exemplary lower extremity device according to one embodiment of the invention.

FIGS. 6E and 6F illustrate a plan view of an unfolded device 600 similar to the device illustrated in FIG. 6B that can be used to improve the profusion and regulate the temperature of patients having different sized extremities 130. As shown in FIGS. 6E and 6F, the design of the device 600 can be deigned to allow various sized extremities 130, as here a foot, to be received and easily positioned within the same sized device 600. By strategic placement use of the enclosing clips 652 (not shown in FIGS. 6E and 6F) the device 600 may be adjusted to fit different sized extremities, such as different sized feet.

In one embodiment, not shown, the device 600 may include one or more body elements 610 each having an internal region 613 and one or more thermal exchange units disposed therein, such as an first body element for forming a first vacuum chamber on the foot portion of a leg and a second body element for forming a second vacuum chamber on the calf portions up to or near a knee of a leg. Alternatively, one single vacuum chamber may be formed into the device 600 for the whole leg portion of a mammal.

Figure 12A:
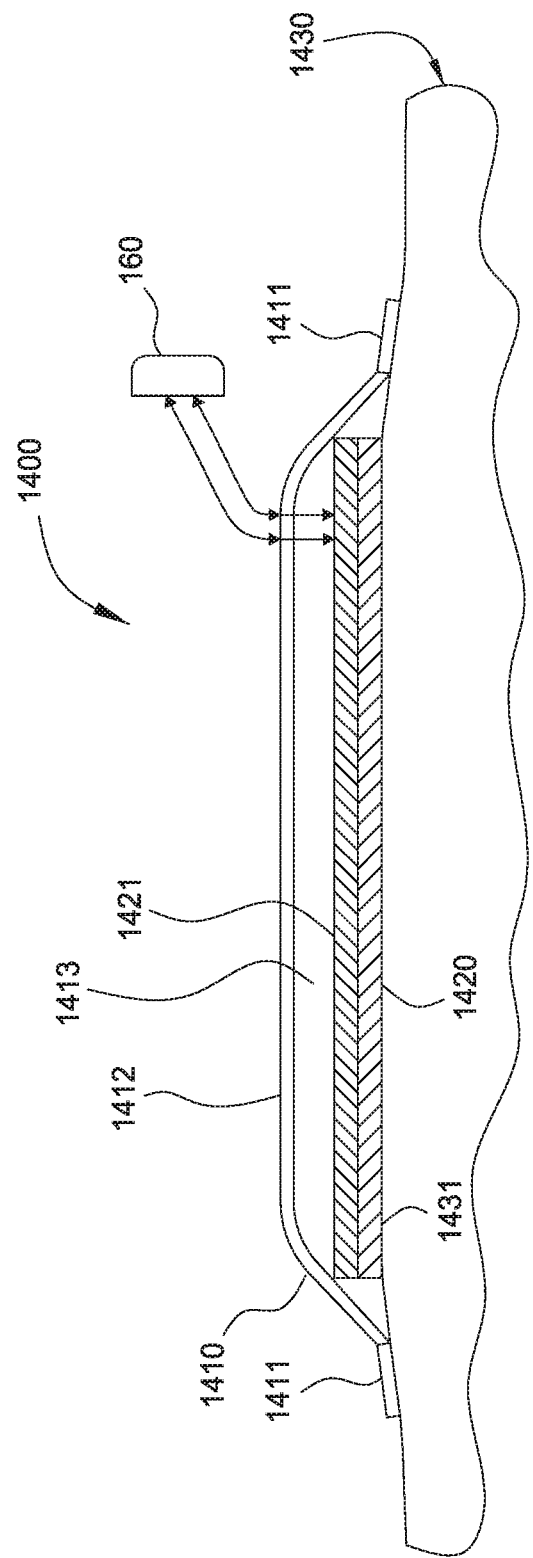
FIG. 12A is a side view of an exemplary device according to one embodiment of the invention.
Figure 12B:
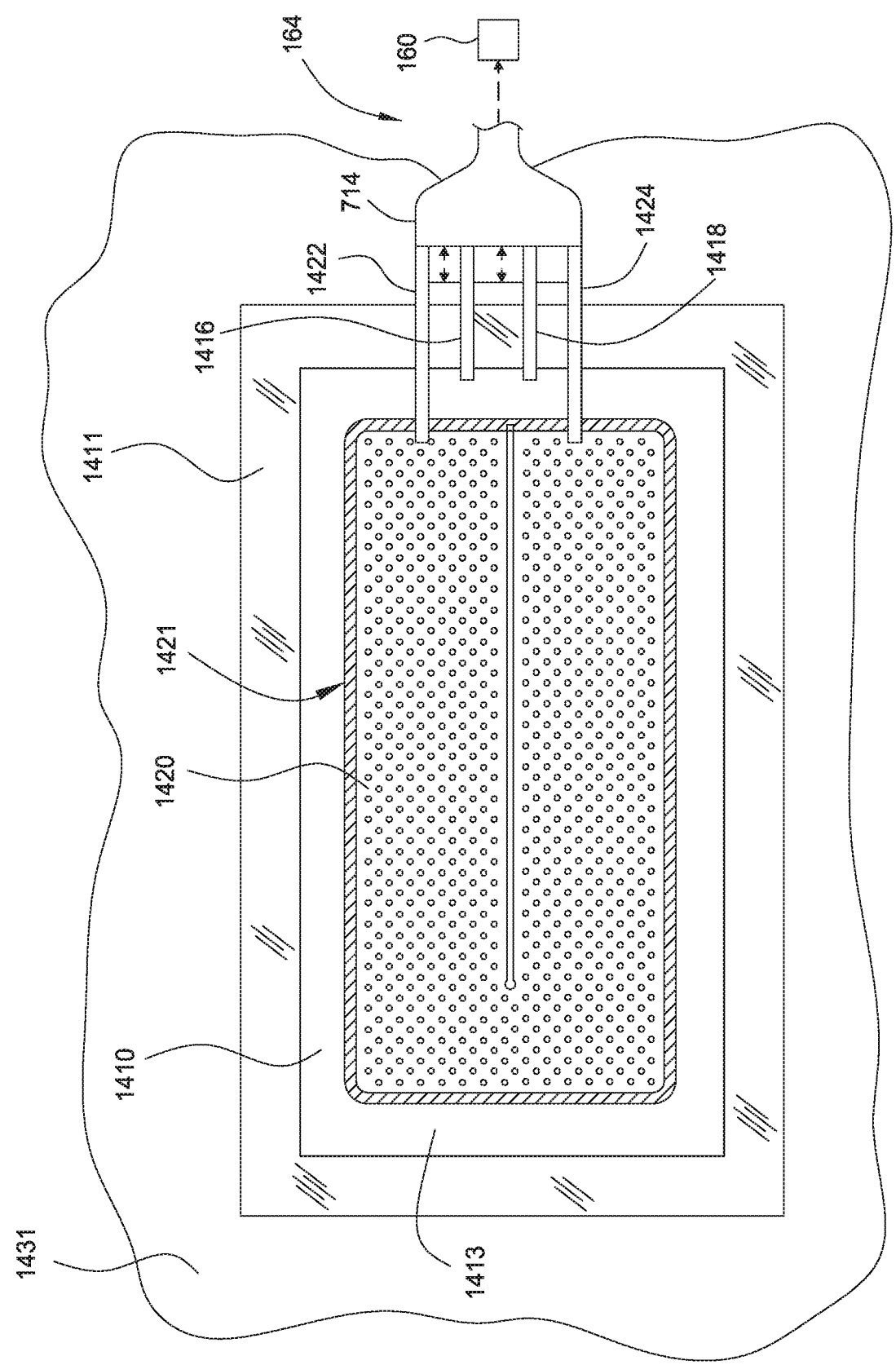
FIG. 12B is a plan view of an exemplary device illustrated in FIG. 12A according to one embodiment of the invention.

FIGS. 12A-12B illustrates an embodiment of the invention in which a device 1400 can be positioned over a desired portion of skin 1431 of a mammal 1430 to increase the blood flow and control the temperature of the mammal 1430. FIG. 12A is a cross-sectional side view of the device 1400 that has been applied to the skin 1431 of a mammal 1430. FIG. 12B illustrates a plan view of the device 1400 that has been applied to the skin 1431 of the mammal 1430. The device 1400 generally contains body element 1410 and one or more thermal exchange units 1420. The body element 1410 generally contains a sealing element 1411 and compliant element 1412. In general, the body element 1410 components can be made of a disposable low cost material, a biocompatible material, a material that can be sterilized, and/or a hypo allergic material similar to the materials discussed above in conjunction with the body element 110. The compliant element 1412 is generally formed from a collapsible and pliant material, including but not limited to, urethane, polyurethane, polypropylenes, polystyrenes, high density polyethylene's (HDPE), low density polyethylene's (LDPE), poly(vinyl chloride), rubbers, elastomers, polymeric materials, composite materials, among others. The compliant element 1412 can be made of a transparent or semi-transparent material that allows viewing of the skin 1431 region of the mammal 1430. The thickness of the compliant element 1412 is not limited as long as it can sustain the pressurized conditions when the device 1400 is used. In one example, a thickness from about 1.5 mils to about 12 mils can be used to pliantly conform to the shape and size of the portion of the skin 1431 contained therein.

The sealing element 1411 is generally used to form a seal to the skin 1431 of the mammal 1430 so as to enclose the one or more thermal exchange units 1420 in an internal region 1413. The sealing element 1411 is generally designed to form a seal between the body element 1410 and the skin to allow a pressurized condition to be applied within the formed internal region 1413 by use of the control system 164 and the other supporting equipment discussed above (e.g., reference numerals 160-163). The sealing element 1411 can be made of a sticky seal material, such as hydrogel, polyurethane, urethane, among others. Another example is a PS series thermoplastic polyurethane from Deerfield Urethane, Inc. Disposable sealing materials may be manufactured and packaged such that they are sterile before use and/or hypoallergenic to meet health and safety requirements. The sealing element 1411 may include an air permeable portion and/or made of a permeable membrane material or a breathable material to permit the flow of air.

The one or more thermal exchange units 1420 are generally similar to the devices discussed above in conjunction with FIGS. 5A-5B. In one embodiment, as shown in FIG. 12A, the one or more thermal exchange units 1420 have an insulating layer 1421 disposed on one or more sides of the device to reduce heat loss to environment away from the skin 1431 and/or improve the heat transfer process to the skin 1431.

Referring to FIG. 12B, during operation the control system 164 components are used to create a pressurized condition in the internal region 1413 by use of the various fluid ports or pressure ports, such as a pressure port 1416, a pressure sensing line 1418, the fluid supply line 1424, and the fluid return line 1422 that pass through one or more apertures formed in the body element 1410. In one embodiment, the internal region 1413 is evacuated by use of a vacuum pump (not shown) that is connected to the pressure port 1416 to create a vacuum condition in the internal region 1413. The sub-atmospheric pressure created in the internal region 1413 will cause the atmospheric pressure external to the device 1400 to urge the compliant element 1412 against the one or more thermal exchange units 1420 and/or skin 1431 to increase the blood flow and control the temperature of the mammal 1430. In this way the device 1400 can be positioned on any open area of the subject, such as positions on a mammal's back, chest, thigh, or neck to increase the blood flow and control the temperature of the subject.

Figure 12C:
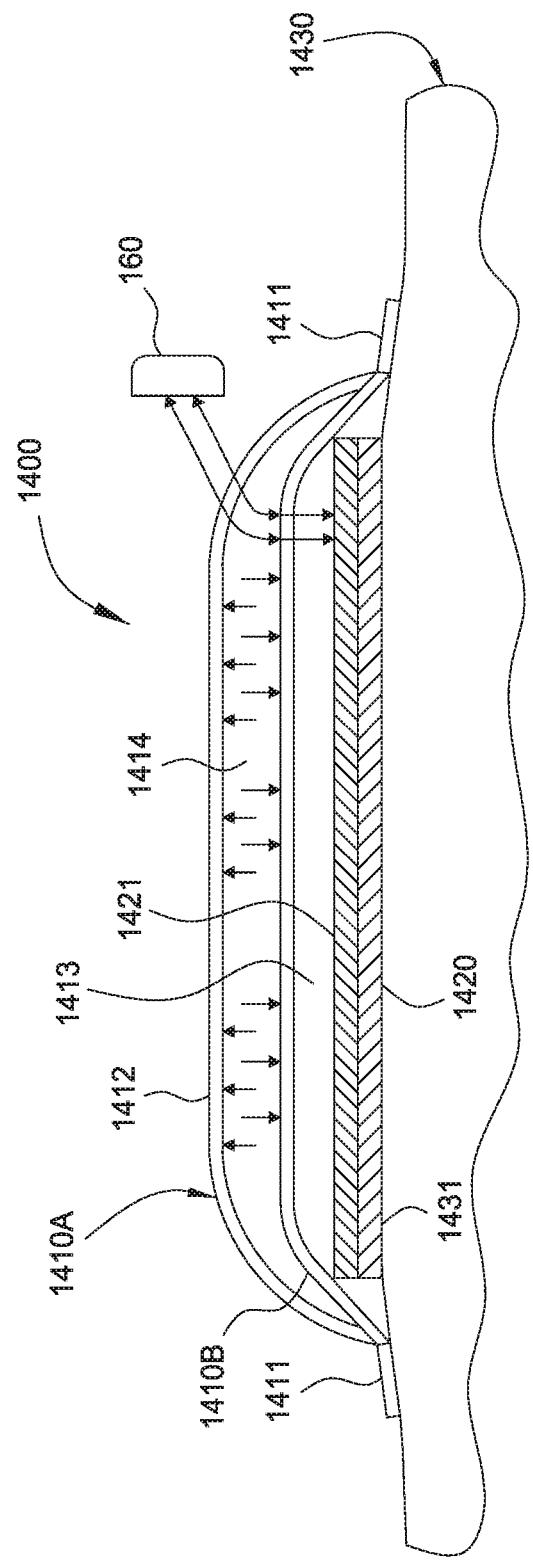
FIG. 12C is a side view of an exemplary device according to one embodiment of the invention.

In another embodiment of the device 1400, as shown in FIG. 12C, the device 1400 contains a second region 1414 that is positioned between a first body element 1410A and a second body element 1410B in which a gas is delivered to achieve a positive pressure therein to cause the second body element 1410B to push against the one or more thermal exchange units 1420 and skin 1431. The pressure delivered in the second region 1414 can be any desirable pressure, such as between about 1 mmHg to about 80 mmHg above atmospheric pressure. In this way the device 1400 can be positioned on any open area of the subject, such as positions on a human's back, chest, thigh, or neck to the blood flow and control the temperature of the subject by application of pressure to the second region 1414 and thermal control of the one or more thermal exchange units 1420.

In one embodiment, the devices, such as devices 100-600 and 1400 may include one or more compression pads around one or more portions of the one or more body elements containing an extremity. In one example, the device 600 includes an inflatable cuff assembly 680 that is positioned around one or more portions of the body element 610. Each inflatable cuff assembly 680 may include one or more air pockets (i.e., internal sealed region within the inflatable cuff assembly 680) that are connected to a fluid tubing 682 and fluid delivery device 681 so that the air pockets can be filled with air or various fluids when the extremity 130 is positioned inside the device 600 to cause a compression force on the extremity 130. In addition, the pressure within the air pockets in the compression pad can controlled using the air or fluids delivered from the fluid delivery device 681 to provide a bellow-like motion to apply various compression pressures or pressurized forces on portions of the extremity 130 intermittedly, consecutively, or otherwise in a time appropriate manner. The one or more thermal exchange units 620 and inflatable cuff assemblies 680 of the device 620 can be positioned in an overlapping configuration or separately on one or more portions of the body element of the device. It is believed that applying pneumatic compression pressure or pressurized force on portions of the extremity 130 may increase blood flow within the leg, prevent clotting and blood pooling in the veins, and prevent deep vein thrombosis. FIG. 6G illustrates is a side view of one embodiment of the device 600, which also contains an inflatable cuff assembly 680 that may be used to compress a portion of the extremity during one or more phases of the treatment process. The inflatable cuff assembly 680 may include an inflatable cuff 683 (e.g., conventional inflatable cuff, flexible bladder), fluid delivery device 681 (e.g., mechanical pump), and a fluid tubing 682 that connects the fluid delivery device 681 and a sealed internal region of the inflatable cuff 683 to allow a delivered fluid to inflate and deflate the inflatable cuff 683 to a desired pressure at a desired time. The inflatable cuff assembly 680 design can be used in conjunction with the other components discussed herein to transfer heat between the extremity and the one or more thermal exchanging devices, and also actively pump blood within the extremity by the use of sequential compression forces applied to the extremity by the inflatable cuff 683 and the fluid delivery device 681 that are in communication with the controller 160.

FIG. 7 illustrates an example of a manifold 714 having one or more fittings that are used to connect the various gas, vacuum or fluid lines to various components internal and external to the device 700 according to one or more embodiments of the invention. The manifold 714 can be attached to the one or more body elements and thermal exchange units of the device through one or more apertures on the body elements and the thermal exchange units. FIG. 7 is a partial cut-away view that schematically illustrates a device 700 that contains the various components discussed above in conjunction with the device 100-600 and 1400 and the manifold 714 is generally useful in any of the configurations discussed herein in. In one aspect, the manifold 714 is used in place of the manifolds 114, 214, 325, 414, and 625 discussed above.

The manifold 714 generally contains one or more fluid ports or pressure ports, such as a pressure port 716, a pressure sensing line 718, a fluid supply line 724, and a fluid return line 722, which can be connected to the manifold body 715 or integrally formed using injection molding, heat stacking, adhesives or other manufacturing methods. Accordingly, quick connect fittings or connectors can be incorporated to provide a connection point to interface the thermal exchange units, fluid pads, other heating components, electric pads, vacuum lines, pressure sensing lines, etc. For example, the manifold 714 may include connectors 730, 732, 734, 736, such as a quick connect type connector similar to CPC Colder Products Company in St, Paul, Minn. In operation, the vacuum space formed in the device 700 requires an robust and airtight seal so that the thermal heat transfer fluids and/or air external to the device doesn't affect the operation of the process. The manifold 714 can be made out of injection molded plastic materials for its low cost, or any other suitable materials. A seal is generally formed between the manifold 714, the various one or more fluid ports or pressure ports (e.g., reference numerals 716, 718), and the body element 710 (e.g., similar to body elements 110, 210) to allow a desired pressure to be reached in the internal region 713 of the device 700 by use of the pump 163. The seal formed between the body element 710 and the various components of the manifold 714 can be created using conventional adhesives, mechanical force, or o-rings to name just a few.

As shown in FIG. 7, the manifold 714 may be connected to the inlet of the thermal exchange units 720A and 720B, which is similar to the devices discussed in conjunction with FIG. 5A-5B, using the fluid supply line 724 through one or more fluid supply fittings 754 and conventional tubing 753 that is in fluid communication with the connector 732 and the fluid supply line 161A of the fluid source 161. The outlet of the thermal exchange units 720A and 720B is connected to the fluid return line 722 through one or more fluid supply fittings 752 and conventional tubing 755 that is in fluid communication with the connector 730 and the return fluid line 161B of the fluid source 161.

In one embodiment, the internal region 713 of the device 700 is connected to the pump 163 which is connected to the pressure port 716 that contains a connector 736 contained in the manifold 714, and a fitting 756 that is disposed within the internal region 713 of the device 700. In one aspect, the internal region 713 of the device 700 may also be connected to the vacuum sensor 162 which is connected to the pressure sensing line 718 that contains a connector 734 that is connected to the manifold 714, and a fitting 758 that is disposed within the internal region 713 of the device 700.

In operation, a hand, a forearm, a foot, a leg, an upper extremity, or a lower extremity (not shown) is disposed within the opening 712 of the device 700 and enclosed within the one or more body elements 710 with one or more thermal exchange units 720A, 720B attached thereon and the manifold 714 attached thereto. Alternatively, the device may need to be assembled by folding, rolling one or more body elements and enclosed with one or more enclosing clips. In addition, one or more detachable thermal exchange units may be pre-assembled inside the device or may be assembled upon disposing an extremity into the device. Then, a vacuum sealing portion 741 of the seal element 740 is wrapped around the opening of the device to form a tight seal and prevent air from entering the space between the extremity and the device.

In one embodiment, a fluid sensing assembly 760 is disposed within the fluid supply line 161A to sense the temperature of the fluid entering the one or more thermal exchange units 720A, 720B so that heating or cooling elements contained within fluid source 161 can be controlled by the controller 160. The fluid sensing assembly 760 generally contains a body 762 and one or more sensors 761 that are in thermal communication with the fluid being delivered to the one or more thermal exchange units 720A, 720B. The one or more sensors 761 may be a thermistor, RTD, thermocouple, or other similar device that can be used to sense the temperature of the fluid flowing through the body 762 and the fluid supply line 161A. It is generally desirable to position the one or more sensors 761 as close to the one or more thermal exchange units 720A, 720B as possible, to assure that the environment will not affect the temperature control of the fluid delivered to the one or more thermal exchange units 720A, 720B.

To control the various aspects of the process of increasing the blood flow and temperature control of a mammal, the controller 160 is adapted to control all aspects of the processing sequence. In one embodiment, the controller 160 is adapted to control the fluid source 161, the pump 163, and all other required elements of the device 700. The controller 160 is generally configured to receive inputs from a user and/or various sensors (e.g., vacuum sensor 162, fluid sensing assembly 760) in the device and appropriately control the components in accordance with the various inputs and software instructions retained in the controller's memory. The controller 160 generally contains memory and a CPU which are utilized by the controller to retain various programs, process the programs, and execute the programs when necessary. The memory is connected to the CPU, and may be one or more of a readily available memory, such as random access memory (RAM), read only memory (ROM), floppy disk, hard disk, or any other form of digital storage, local or remote. Software instructions and data can be coded and stored within the memory for instructing the CPU. The support circuits are also connected to the CPU for supporting the processor in a conventional manner. The support circuits may include cache, power supplies, clock circuits, input/output circuitry, subsystems, and the like all well known in the art. A program (or computer instructions) readable by the controller 160 determines which tasks are performable in the device. Preferably, the program is software readable by the controller 160 and includes instructions to monitor and control the process based on defined rules and input data.

Figure 8:
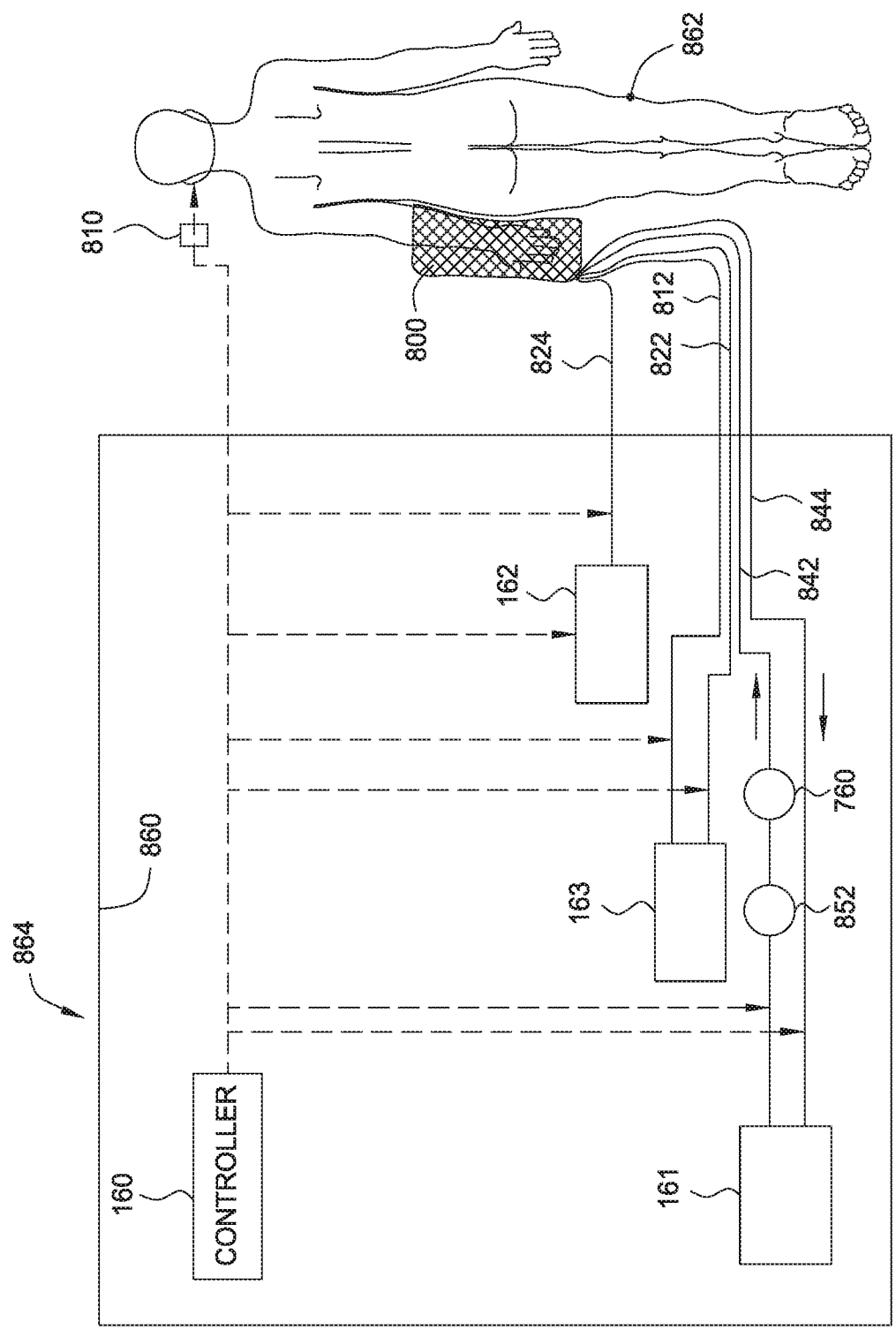
FIG. 8 illustrates one embodiment of a control unit connected to a device according to an embodiment of the invention.

FIG. 8 illustrates one embodiment of the control system 864 that is connected to various parts of a device 800 according to an embodiment of the invention. The device 800 and control system 864 is similar to the devices (e.g., reference numbers 100-700) and control system 164 discussed above in conjunction with FIGS. 1-7. The control system 864 generally contains a controller module 860 having the controller 160 therein that houses all the electronics and mechanical parts which are required to regulate the temperature, vacuum pressure level, and compression pressurized force provided to the pressurized volume of the device. In this configuration, the control system 864 typically includes, for example, a pump 163, a vacuum sensor 162, conventional tubing 824, a fluid source 161, a fluid flow sensor 852, a fluid sensing assembly 760, and a temperature sensor 810. The temperature sensor 810 is generally a device that is used to measure the temperature of the patient while the process of increasing the blood flow and controlling the temperature of the patient is being performed. Temperature of the patient can be measured in the ear, mouth, on the skin, or rectally using an appropriate conventional temperature sensing device. The control system 864 may also contain a thermal exchange medium pump, a heater, a cooler, thermocouples, a heating medium pump, a proportional-integral-derivative (PID) controller for process control of the vacuum and the temperature, one or more power supplies, display panels, actuators, connectors, among others, that are controlled by the controller 160. The settings and current readings of the various elements in the of the control system 864 may be conveniently positioned onto a display panel (e.g., lighted display, CRT) which provides an operator interface. The controller 160 may contain additional electronics for optimal operation of the device 800 of the invention. In alternative embodiments, the vacuum control and temperature control may be controlled by two different controllers.

The control system 864 may provide safety features including a device shutdown feature that is activated if the device sensors, such as the temperature and pressure sensors, fail or become disconnected. The control system 864 may also include an alarm circuit or an alert signal if the temperature of the apparatus is not regulated correctly. A relief valve may be provided within the vacuum loop of the device such that the chamber may be vented if the vacuum within the chamber exceeds a certain level.

In one embodiment, a temperature probe 862 can be provided to measure the temperature of a portion of a mammal other than a foot, leg, or other extremity where the device is attached to. In another embodiment, a tympanic membrane can be attached to the ear canal as a temperature sensor 810 to provide core temperature reading. As such, a reference temperature for the human, such as a patient, can be obtained. Other sensors may include patient's blood flow and blood pressure and heart rate. These data are important to proper patient health care keeping the patient at normal temperature range and from various thermal maladies. The temperature of the skin in the device could be measured to indicate if the body portion is in a state of vasoconstriction or vasodilatation or what temperature the skin is compared two device fluid temperatures. Temperature of the skin can be measured by different means and different devices like Thermocouples, Thermistor, Heat flux and other measuring devices. Blood flow rate could also be measured and data sent to the controller 160.

As shown in FIG. 8, the device 800 can be connected to the pump 163 (e.g., mechanical vacuum pump, pump and vacuum ejector) via a vacuum port 812 and a vacuum sensor return line 822 to provide a vacuum pressure or a negative pressure inside the device 800. It is important to maintain the vacuum and/or negative pressure levels and correctly sense and read out the vacuum/pressure levels inside the device where the extremity is exposed to and send the data to a vacuum transducer mounted in the controller 160. The vacuum transducer could also be located in the manifold 714 (FIG. 7) allowing for a better response and more accurate control of the vacuum levels. The signal controlling the vacuum pump would come through wires from the vacuum transducer to control circuits in the controller 160. Additional set of data, such as pressure data applied to the extremity by the vacuum, could be measured through a series of pressure sensors placed through the device to record pressure levels and send data to the controller 160 for evaluation. The controller 160 can then adjust the levels of vacuum and the temperature within the device to produce the highest level of blood flow and to increase the body's core temperature as needed.

In addition, the device 800 with one or more thermal exchange units therein may be connected to the fluid source 161 via a thermal exchange medium supply line 842 and a thermal exchange medium return line 844. Further, the flow of a thermal exchange medium flown inside the thermal exchange medium supply line 842 can be monitored and regulated by the fluid flow sensor 852 and/or fluid sensing assembly 760. In addition, a low fluid led may be used and displayed on the front panel of the controller 160 to warn an operator of fluid level in the reservoir of a fluid source. Additional sensor will be added to the fluid reservoir to send a signal when the fluid level is low and more fluid is needed. Further, there may be controlling signal that allow a conventional fluid pump to operate in a mode of returning fluid back from the fluid pads when the procedure or a single operation of the device is complete. Additionally, the device may include a temperature sensor for the heated or cooled fluid circulating through various tubing's and fluid lines. In addition, the thermal exchange units of the invention may include one or more temperature sensors and thermocouples to monitor the temperature of a mammal's extremity and provide temperature control feedback.

These lines and ports of the invention may be bundled, contained, and strain-relieved in the same or different protective sheaths connected to the controller 160. The lines may also be contained in the same or different tubing set with different enclosures for each medium used, such as fluid, vacuum, electric heat, and air lines.

In one embodiment, the thermal exchange units are coupled in a closed loop configuration with the fluid source 161 which provides a thermal exchange medium. For example, the thermal exchange unit may be coupled in a closed liquid loop configuration with a liquid tank housed within the controller module 860. In one embodiment, one or more resistive heating elements and/or thermoelectric devices are used to heat or cool the thermal exchange medium contained in the liquid tank. The closed loop configuration reduces the maintenance requirements for the operator because it minimizes the loss of thermal exchange medium that typically occurs if the thermal exchange unit is detached from the thermal exchange medium source. Contamination of the thermal exchange medium source is also minimized by the closed loop configuration. Contamination of the thermal exchange medium such as water can also be reduced by adding an antimicrobial agent to the thermal exchange medium source. In different embodiments, the thermal exchange medium may be either a liquid or a gas. In practice, the thermal exchange medium flow rate should be as high as possible. It was found through testing that the inflow temperature and the outflow temperature through the pad should be within about <1.0° C. It has also been found that, in certain cases, blood flow did not increase at all if the pad fluid temperature was below 40° C. A high flow rate allows better temperature consistency, results in less thermal loss, and creates better thermal exchange. In a closed loop configuration including the thermal exchange unit and the thermal exchange medium source, with a total system volume (e.g., 0.75 liters), a flow rate (e.g., 2 liters per minute) transfers as much fluid through the thermal exchange unit (e.g., twice than a flow rate of 0.35 liters per minute).

In an alternative embodiment, the thermal exchange unit and vacuum lines may be connected to the controller 160 using actuated fittings such as quick connect fittings with an automatic shut off mechanism. The automatic shut off mechanism halts the vacuum application and the heating medium flow as soon as the vacuum lines are disconnected. Actuated fittings may also allow the operator to change thermal exchange units. In addition, various quick disconnect connectors may be added to the controller 160 to allow various disposable parts of the device to be disconnected after each use.

The embodiments of the apparatus described above provide a method of increasing blood flow in one or more extremities of a mammal and decreasing clots within the veins in order to regulate thermal maladies and/or prevent deep vein thrombosis (DVT). The method includes providing one or more devices of the invention to the mammal and regulating the temperature of the one or more extremities of the mammal using the devices. As a result, one or more Arteriovenous Anastomoses (AVAs) blood vessels inside an extremity of a mammal are vasodilator, and constriction of the AVA blood vessels is reduced, thereby increasing blood flow and blood volume in the one or more extremities, decreasing the vessel wall contact time of the blood flow, and decreasing clots in the veins due to pooling. Any suitable portions of an extremity, preferably an extremity with vasculature that can be vasodilator by the device, may be placed into a device and sealed therein.

Referring to FIG. 2, the process of using the device 200 discussed above generally starts by positioning an extremity 130 in the internal region 213 of the device 200. While the process of increasing blood flow and the temperature of a mammal is discussed in conjunction with the device 200, this configuration is not intended to be limiting to the scope of the invention since any of the devices discussed herein could be used to perform this process. Once the extremity 130 is enclosed in the device 200, negative pressure is applied to a pressure port 116 thereby lowering the pressure within the internal region 213 and exposing the extremity 130 to decreased pressure in the range, for example, of about 0 to about −20 mmHg, such as from about −10 mmHg to about −14 mmHg. Simultaneously or sequentially, a thermal exchange medium is introduced into one or more thermal exchange units 220 positioned inside the internal region 213 of device 200. The flow rate of the pump 163 may be constant and the flow rate need only be to maintain so that a constant pressure can be achieved in the internal region 213. If there is a slight leak in the system the required flow rate may be greater than about 6 liters per minute, and is preferably about 4 liters per minute or lower. In one aspect, the flow rate of the vacuum pump may be between about 4 liters and about 10 liters per minute, but is preferably less than about 6 liters per minute.

In one embodiment, the controller 160 manages the thermal exchange medium and negative pressure for the duration of the treatment, which may be about 30 minutes, for example. The duration may be longer or shorter depending on the size of the extremity treated and the temperature of the extremity. The process may be repeated one or more times as needed. In some cases, the duration of the treatment may be cycled "on" for a period of time and then "off" for a time period. In one example, the duration of the treatment is about 1 minute or longer and then off for a period of about 1 minute or longer, which is repeated for 5 cycles or more. The controller is configured to halt the treatment after each treatment period. A "stop" button on the control unit may be used to turn off both the thermal exchange medium supply and the vacuum. In one aspect, the controller 160 is designed to monitor the expansion of the lower limb to determine venous refilling so that the refill time can be adjusted as desired. In general, only small amounts of pressure are needed to be supplied to the extremity to cause movement of blood within the extremity, such as between −3 mmHg and about −20 mmHg. In one example, the one or more thermal exchange units 220 are brought into contact with the extremity by applying a negative pressure of about −3 mmHg within the internal region to provide good contact for thermal exchange units, and then the pressure in the internal region is increased to about −20 mmHg for 30 seconds to increase the pressure on the extremity and cause the blood to be pumped. The pressure applied to the extremity can then be cyclically varied between a lower pressure and a higher pressure level for a desired number of times. When the cycled pressure drops to a low pressure (e.g., −3 mmHg) level this provide time for venous refilling.

Embodiments of the invention may be used to increase blood flow and regulate the temperature of a mammal by increasing the temperature of the thermal exchange medium delivered to the thermal exchange devices to a temperature as high as possible without burning the mammal. In a healthy patient, burning of the cells on the appendage can occur if the cell temperature exceeds about 43 degrees Celsius (° C.), but this may vary with exposure time and rate of thermal transfer. Therefore, the temperature of the thermal exchange medium is preferably calibrated such that skin temperature is maintained at less than 43 degrees Celsius. For example, different people have different tolerance levels for different temperature ranges, according to their ages, health conditions, etc. In general, to heat the extremity it is desirable to control the temperature of the thermal exchange medium and thus the surface of the thermal exchange units to a temperature is between about 30° C. to about 43° C. In one embodiment, the temperature of the thermal exchange medium and thus the surface of the thermal exchange units is between about 37° C. to about 40° C.

In addition, the device can be used to cool the temperature of a patient. In general, a patient's temperature can be maintained, or, if it is required by the procedure, the patient's core temperature can be lowered by active cooling to about 33° C. In general, to cool the extremity it is desirable to control the temperature of the thermal exchange medium and thus the surface of the thermal exchange units to a temperature is between about 0° C. to about 30° C. In one embodiment, the temperature of the thermal exchange medium and thus the surface of the thermal exchange units is between about 0° C. to about 10° C.

Consequently, in order to reduce patient discomfort, the controller may be configured with different temperature and vacuum settings. In one embodiment, one treatment setting is "High", which includes the highest temperature and negative pressure setting. "Medium" and "Low" settings have progressively lower settings for temperature and/or pressure. Patients who are being treated for an extended amount of time or who are at high risk for additional complications may be treated on the "Low" setting. The pressure setting may be adjusted to provide positive or negative pressure in patients. For example, extra care is provided for applying pressure and thermal regulation to patients who are under anesthesia. In one embodiment, the high temperature is about 42° C., the medium temperature is about 41° C., and the low temperature is 40° C., while the vacuum level remains at about −10 mmHg for all temperature settings.

In a further aspect, the device may use between about 5 watts and about 250 watts of power to raise a body core temperature at a rate of between about 4° C./hour and about 12° C./hour. Preferably, the power applied is between about 5 watts and about 80 watts, although a power of up to about 250 watts may be used. In contrast, conventional convective warming blankets that heats the whole body may use about 500 watts, which is harder to control and is less efficient.

Table 1 illustrates exemplary suitable applied power (in watts) as compared to contact surface area. In one embodiment, the surface of contact between the thermal exchanging units (e.g., reference numerals 120A, 120B, 220, 320A, 320B) and the skin of the extremity is between about 30 in$^2$ (e.g., 0.019 m$^2$) and about 410 in$^2$ (e.g., 0.264 m$^2$). In another embodiment, the surface of contact between the thermal exchanging units and the skin of the extremity is less than about 800 in$^2$ (e.g., 0.516 m$^2$). In general, it is desirable to maximize the contact between the thermal exchanging units and the skin of the extremity to improve heat transfer. However, it is through the use of the AVAs that are primarily found in the extremities that provide the most efficient and controlled heat transfer between the extremity and the thermal exchanging units.

TABLE 1

|  | 1 | 2 | 3 | 4 | 5 | 6 | 7 | 8 |
|---|---|---|---|---|---|---|---|---|
| % Area | 1.25% | 2.5% | 4.86% | 3.62% | 8.28% | 16.56% | 10.25% | 13.48% |
| Area sq. inch | 37.5 | 75.0 | 145.8 | 108.6 | 248.4 | 496.8 | 307.5 | 404.4 |
| Watt/sq. inch | 0.32 | 0.32 | 0.24 | 0.32 | 0.24 | 0.24 | 0.16 | 0.16 |
| Watts | 12.0 | 24.0 | 35.0 | 34.8 | 59.6 | 119.2 | 49.2 | 64.7 |
| Watts to Core | 6.0 | 12.0 | 17.5 | 17.4 | 29.8 | 59.6 | 6.2 | 32.4 |

The testing as described herein was done in lab using a prototype of the device as shown in FIG. 1A. The percentage (%) increase per minute in the local blood volume of the extremity was measure. Volunteer human subjects were participated in the study. The "% Area" row illustrates the percentage of area of the patients body covered by the thermal exchanging units (e.g., reference numeral 120A, 120B in FIG. 1A, reference numeral 220 in FIG. 2) used to perform the process. The "Area sq. inch" row illustrates the actual square inches covered by the thermal exchanging units. The "Watt/sq. inch", "Watts", and "Watt to Core" are examples of the power and power densities used in exemplary versions of the devices discussed herein. The columns labeled "1"-"8" illustrate different thermal exchanging unit and device configurations.

Figure 9:
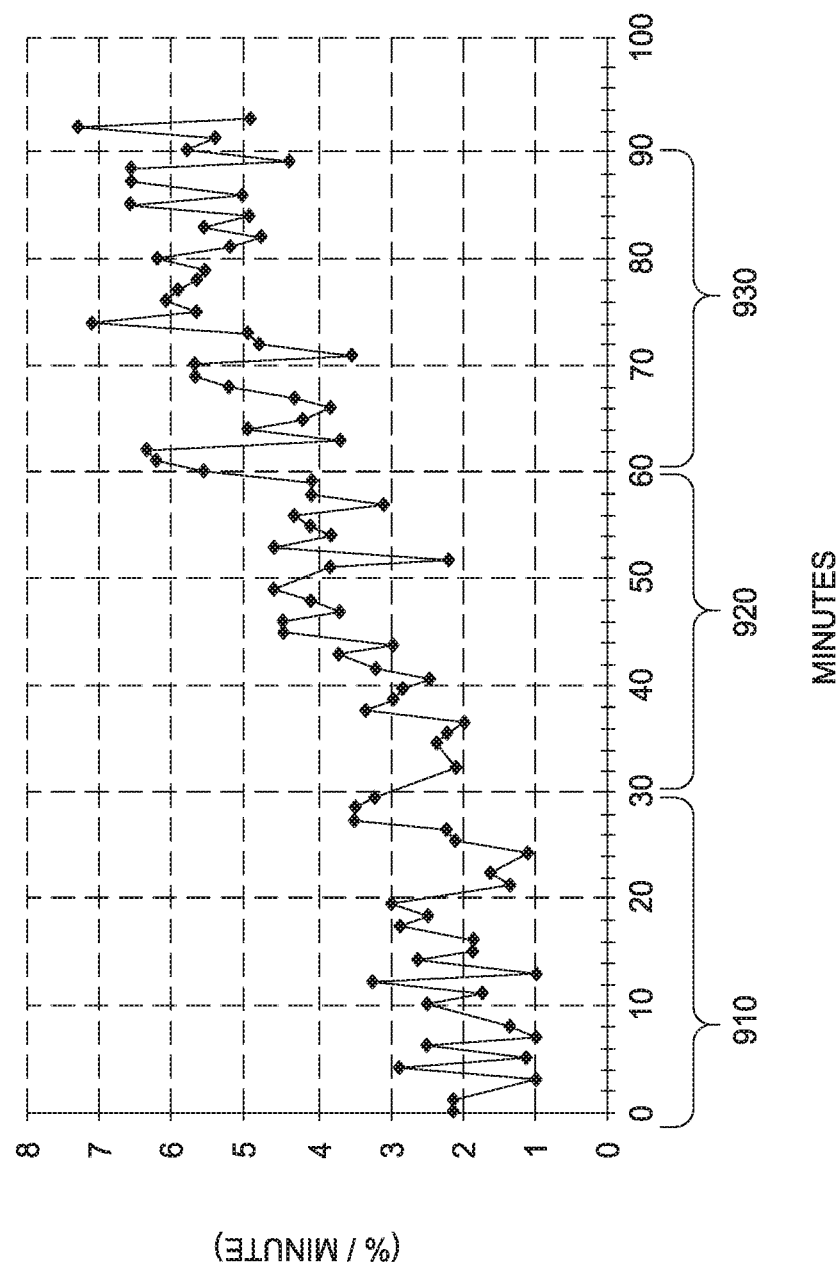
FIG. 9 is a graph demonstrating the results of increased blood flow using the device according to one embodiment of the invention.

FIG. 9 is a graph demonstrating the results of increased blood flow using the device 100 according to one embodiment of the invention. The results were achieved on a female subject using the device shown in FIG. 1A. The baseline readings 910 were taken from zero to about 30 minutes on the time scale, no device was used during base line readings. The readings 920 from about 30 minutes to about 60 minutes with the device "on" and set to a vacuum level of about −10 mmHg was maintained in the internal region 113, and a thermal exchange medium temperature of about 42° C. was delivered to the thermal exchange units 120A, 120B. The readings 930 from about 60 minutes to about 90 minutes the vacuum setting with the device was set to about −10 mmHg was maintained in the internal region 113, and a thermal exchange medium temperature of about 42° C. was delivered to the thermal exchange units 120A, 120B. The results show an increase in blood flow from a baseline of about 1% per minute to about 3% per minute to maximum readings between about 6% to about 7% during the test.

Figure 10:
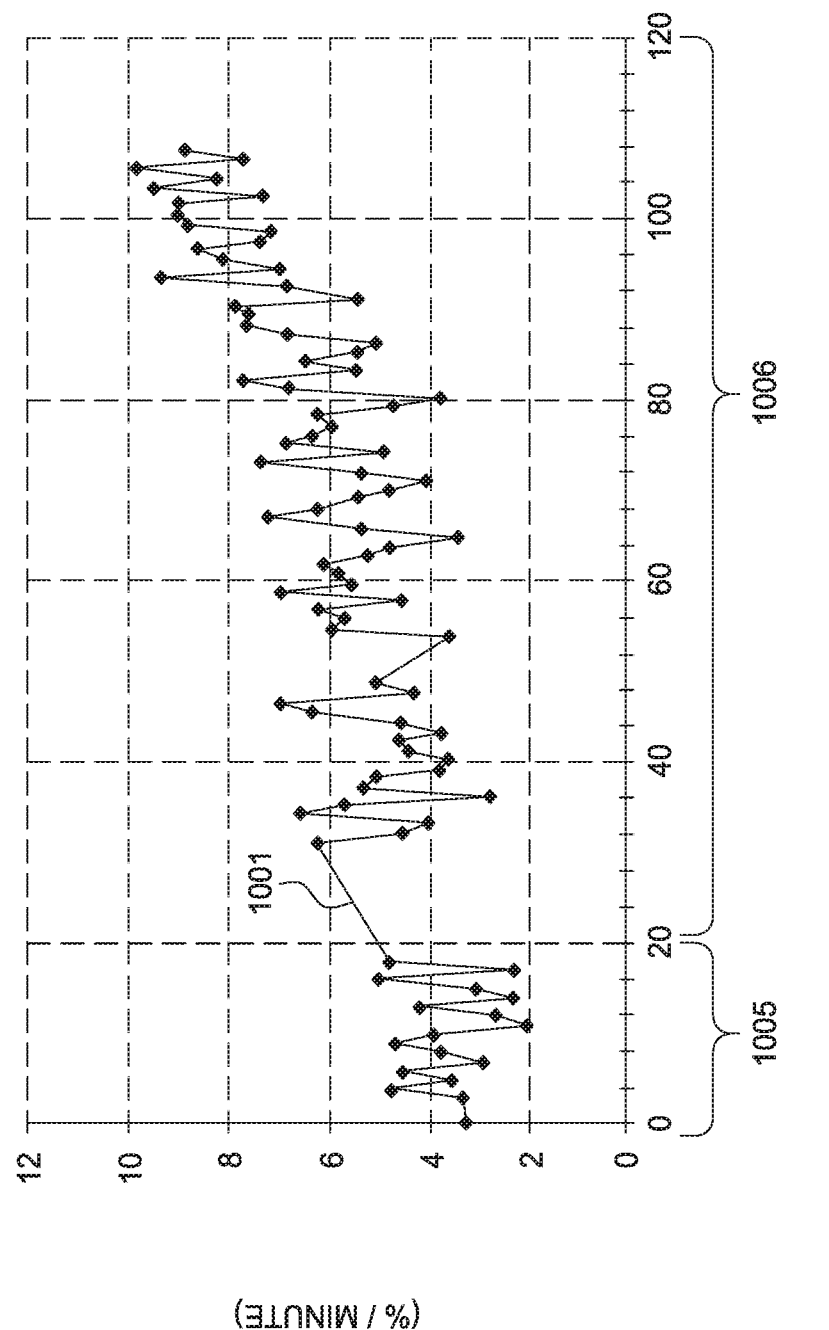
FIG. 10 is another graph demonstrating the results of increased blood flow using the device according to another embodiment of the invention.

FIG. 10 is another graph demonstrating the results of increased blood flow using the device according to another embodiment of the invention. This is a male subject. The baseline readings 1005 were taken from zero to about 20 minutes on the time scale. The readings 1006 from about 30 minutes to about 110 minutes were with device "on" while a vacuum level of about −10 mmHg was maintained in the internal region 113, and a thermal exchange medium temperature of about 42° C. was delivered to the thermal exchange units 120A, 120B. The results show an increase in blood flow from a baseline of about 2% to about 4.2% per minute to maximum of about 8% per minute to about 10% during the test.

Figure 11:
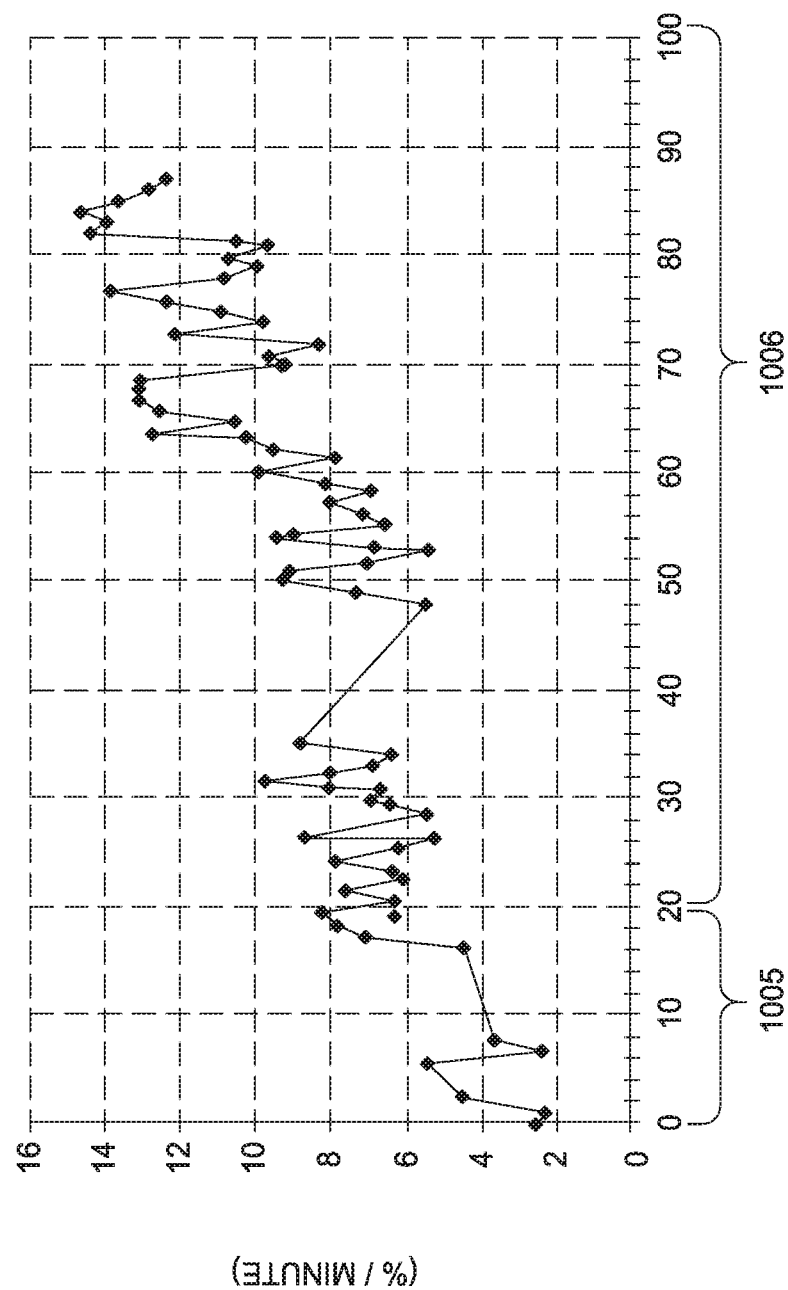
FIG. 11 is another graph demonstrating the results of increased blood flow using the device according to yet another one embodiment of the invention.

FIG. 11 is another graph demonstrating the results of increased blood flow using the device according to yet another one embodiment of the invention. This is a female subject; the device was as shown in FIG. 1A. The base line readings 1005 were taken from zero to about 15 minutes. The device was "on" from about 15 minutes to about 60 minutes while a vacuum level of about −10 mmHg was maintained in the internal region 113, and a thermal exchange medium temperature of about 42° C. was delivered to the thermal exchange units 120A, 120B using the device as shown in FIG. 1A. From about 60 minutes to about 85 minutes the vacuum level was set to about −10 mmHg and a thermal exchange medium temperature of about 42° C. was delivered to the thermal exchange units 120A, 120B. The results show an increase in blood flow from baseline of about 2% per minute to about 4.5% per minute to maximum readings of about 12% to about 14% during the test.

While the foregoing is directed to embodiments of the present invention, other and further embodiments of the invention may be devised without departing from the basic scope thereof, and the scope thereof is determined by the claims that follow.

What is claimed is:

1. A device for increasing blood flow, controlling body temperature, and/or reducing a risk of deep vein thrombosis (DVT) in a mammal, comprising:
   a flexible body having one or more flexible walls that enclose at least a portion of an internal region, wherein the flexible body defines an outermost surface of a portion of the device that is disposed over a first portion of an extremity of the mammal
   wherein the flexible body is adapted to receive the first portion of the extremity of the mammal and allow the first portion of the extremity to be positioned within the internal region;
   a pump fluidly coupled to the internal region and configured to create a pressure below atmospheric pressure within the internal region causing atmospheric pressure external to the flexible body to urge the flexible body against the first portion of the extremity of the mammal disposed in the internal region, wherein the flexible body is configured to substantially conform to a shape of the first portion of the extremity when the pump creates the pressure below atmospheric pressure within the internal region; and
   one or more compression pads configured to apply a positive force to the extremity of the mammal when the one or more compression pads disposed over the first portion or a second portion of the extremity and filled with a fluid.

2. The device of claim 1, wherein the pump comprises a vacuum ejector or mechanical vacuum pump that is configured to create a pressure in the internal region between about −3 mmHg and about −80 mmHg relative to the pressure external to the flexible body.

3. The device of claim 1, further comprising one or more thermal exchanging units that are in thermal communication with the internal region.

4. The device of claim 3, further comprising a fluid source that is in fluid communication with a heat exchanging plenum in one of the one or more thermal exchanging units.

5. The device of claim 3, further comprising a controller unit connection to the pump, and a fluid source coupled to the one or more thermal exchanging units.

6. The device of claim 1, wherein the extremity is a leg of the mammal.

7. A device for increasing blood flow, controlling body temperature, and/or reducing a risk of deep vein thrombosis (DVT) in a mammal, comprising:
   a flexible body having one or more flexible walls that enclose at least a portion of an internal region, wherein at least a portion of the flexible body defines an outermost surface of a portion of the device that is disposed over a first portion of an extremity of the mammal, and the flexible body comprises:
      an opening formed in the flexible body that is adapted to receive the extremity of the mammal and allow the first portion of the extremity to be positioned within the internal region; and
      a first flexible compliant layer that is sealably bonded to a second flexible compliant layer, wherein the sealably bonded first and second flexible compliant layers:
         form a fluid plenum having a fluid plenum region disposed between the first and the second flexible compliant layers; and
         define at least a portion of the internal region which is separated from the fluid plenum region by at least a portion of the first flexible compliant layer, wherein the flexible body is configured to substantially conform to a shape of the first portion of the extremity when a pump creates pressure below atmospheric pressure within the internal region; and
   one or more compression pads configured to apply a positive force to the extremity of the mammal when the one or more compression pads are disposed over the first portion or a second portion of the extremity and filled with a fluid.

8. The device of claim 7, further comprising one or more tubes coupled to an aperture formed in the flexible body, wherein one of the one or more tubes is in fluid communication with the internal region.

9. The device of claim 8, wherein one of the one or more tubes is in fluid communication with a vacuum pump and one of the one or more tubes is in fluid communication with a fluid delivery system.

10. The device of claim 7, further comprising a manifold assembly which has a plurality of ports that each have a first end and a second end, wherein the manifold assembly is sealably bonded to a surface of the flexible body and the first end of one of the plurality of ports is in fluid communication with the internal region.

11. The device of claim 7, further comprising:
   a fluid source that is in fluid communication with the fluid plenum region; and
   a controller unit that is configured to control the pump and the fluid source.

12. The device of claim 7, further comprising a fluid source that is in fluid communication with the fluid plenum region.

13. The device of claim 7, wherein the flexible body comprises a material selected from the group consisting of urethane, polyurethane, polypropylenes, polystyrenes, high density polyethylene, low density polyethylene, and polyvinyl chloride.

14. The device of claim 7, wherein the internal region is formed by
- sealably bonding a first portion of the first flexible compliant layer to a second portion of the first flexible compliant layer, or
- sealably bonding the first portion of the first flexible compliant layer to a first portion of the second flexible compliant layer.

15. The device of claim 7, wherein the one or more compression pads comprise an internal pocket region that is disposed over the first portion or the second portion of the extremity.

16. The device of claim 7, wherein the one or more compression pads comprise an inflatable cuff that is configured to receive a fluid from a pressure controlling device to adjust the pressure in an internal region of the inflatable cuff.

17. The device of claim 7, wherein the extremity is selected from the group consisting of a hand, a forearm, a forearm with an elbow, a hand with a wrist, a foot, a leg, a calf, and an ankle.

\* \* \* \* \*